United States Patent [19]

Dean et al.

[11] Patent Number: 5,378,703

[45] Date of Patent: * Jan. 3, 1995

[54] SULFONAMIDES USEFUL AS CARBONIC ANHYDRASE INHIBITORS

[75] Inventors: Thomas R. Dean, Weatherford; Hwang-Hsing Chen; Jesse A. May, both of Fort Worth, all of Tex.

[73] Assignee: Alcon Laboratories, Inc., Fort Worth, Tex.

[ * ] Notice: The portion of the term of this patent subsequent to Aug. 31, 2010 has been disclaimed.

[21] Appl. No.: 19,011

[22] Filed: Feb. 18, 1993

Related U.S. Application Data

[63] Continuation-in-part of Ser. No. 775,313, Oct. 9, 1991, Pat. No. 5,240,923, which is a continuation-in-part of Ser. No. 618,765, Nov. 27, 1990, Pat. No. 5,153,192, which is a continuation-in-part of Ser. No. 506,780, Apr. 9, 1990, abandoned.

[51] Int. Cl.$^6$ ............... C07D 513/04; A61K 31/54
[52] U.S. Cl. ......................... 514/222.8; 544/48
[58] Field of Search .................. 544/48; 514/222.8

[56] References Cited

U.S. PATENT DOCUMENTS

| | | | |
|---|---|---|---|
| 4,619,939 | 10/1986 | Maren | 514/363 |
| 4,731,368 | 3/1988 | Hoffman, Jr. et al. | 514/301 |
| 4,746,745 | 5/1988 | Maren | 548/139 |
| 4,797,413 | 1/1989 | Baldwin et al. | 514/432 |
| 4,847,289 | 7/1989 | Baldwin et al. | 514/445 |

FOREIGN PATENT DOCUMENTS

| | | |
|---|---|---|
| 661731 | 4/1963 | Canada . |
| 1516024 | 6/1978 | United Kingdom . |

OTHER PUBLICATIONS

"The Reactions of Some Thiophene Sulfonyl Derivatives," Cremyln et al., *Phosphorus and Sulfur*, vol. 10, pp. 111-119, 1981.

"Studien in der Thiophenreihe. XXIV.$^2$ Uber Nitrothiophene and Thiophensulfochloride," Steinkopf et al., *Justus Liebigs Analen Der Chemie*, vol. 501, pp. 174–186, 1933.

"Heterocyclic Disulphonamides and Their Diuretic Properties," deStevens et al., *Journal of Medicinal and Pharmaceutical Chemistry*, vol. 1(6), pp. 565–576, 1959.

Gronowitz et al., *Thiophene and its Derivatives*, vol. 44, Pt. 3, pp. 135–307 (1986).

*Primary Examiner*—John M. Ford
*Attorney, Agent, or Firm*—Sally Yeager

[57] ABSTRACT

Sulfonamides and pharmaceutical compositions containing the compounds useful in controlling intraocular pressure are disclosed. Methods for controlling intraocular pressure through administration of the compositions are also disclosed.

14 Claims, No Drawings

SULFONAMIDES USEFUL AS CARBONIC ANHYDRASE INHIBITORS

This application is a continuation-in-part of U.S. Pat. application Ser. No. 07/775,313, filed Oct. 9, 1991, now U.S. Pat. No. 5,240,903, which is a continuation-in-part of U.S. Pat. application Ser. No. 618,765, filed Nov. 27, 1990, now U.S. Pat. No. 5,153,192, which is a continuation-in-part of U.S. Pat. application Ser. No. 506,780, filed Apr. 9, 1990, now abandoned.

Field of the Invention

The present invention relates to new sulfonamides useful in lowering and controlling intraocular pressure.

BACKGROUND OF THE INVENTION

Glaucoma is a disease of the eye which is characterized by a progressive loss of visual field due to irreversible damage to the optic nerve to the point where if untreated can result in total blindness. This loss of visual field, in one form of primary open angle glaucoma, or POAG, is associated with a sustained increase in the intraocular pressure (IOP) of the diseased eye. Moreover, elevated intraocular pressure without visual field loss is thought to be indicative of the early stages of this form of POAG.

There are a number of therapies that target reducing the elevated IOP associated with this form of POAG. The most common feature the topical administration of a beta adrenergic antagonist or a muscarinic agonist. These treatments while effective in lowering IOP can also produce significant undesirable side effects.

Another less common treatment for this form of POAG is the systemic administration of carbonic anhydrase inhibitors. However, these drugs also can bring about unwanted side effects, such as nausea, dyspepsia, fatigue, and metabolic acidosis.

U.S. Pat. Nos. 4,797,413, 4,847,289 and 4,731,368 disclose topically dosed thiophene sulfonamides which lower IOP by inhibiting carbonic anhydrase.

Thiophene bis-sulfonamides, which are carbonic anhydrase inhibitors useful for treating conditions attributable to a restriction of blood flow to the brain, including atherosclerosis, occlusion of blood vessels in the brain, stroke and other cerebra vascular diseases, are disclosed in the British Patent No. 1,516,024. Similar compounds are also disclosed in *Justus Liebigs Annalen der Chemie*, 1933, 501, 174–188 and in Phosphorus Sulfur, 1981, 10(1), 111–119.

Other thiophene bis-sulfonamides, which are carbonic anhydrase inhibitors useful as diuretics, are disclosed in the German Patent No. 1,096,916 and *Journal of Medicinal and Pharmaceutical Chemistry*, 1959, 1(6), 565–576.

The compounds of the present invention are new sulfonamides which are carbonic anhydrase inhibitors useful for lowering IOP without producing significant systemic side effects when delivered topically to the eye.

SUMMARY OF THE INVENTION

The present invention is directed to new sulfonamides which can be used to lower and control IOP. The compounds are formulated in pharmaceutical compositions for delivery.

The invention is also directed to methods for lowering and controlling IOP by the administration of the compositions comprising the sulfonamides of the present invention. The compositions can be administered systemically and/or topically to the eye.

DETAILED DESCRIPTION OF THE INVENTION

The sulfonamides of the present invention have the following structure.

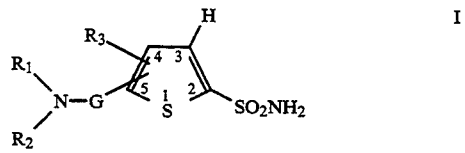

or a pharmaceutically acceptable salt thereof wherein:

$R_1$ is H; $C_{1-4}$ alkyl; $C_{2-4}$ alkyl substituted optionally with OH, halogen, $C_{1-4}$ alkoxy or $C(=O)R_7$.

$R_2$ is H; $C_{1-8}$ alkyl; $C_{2-8}$ alkyl substituted with OH, $NR_5R_6$, halogen, $C_{1-4}$ alkoxy, $C_{2-4}$alkoxy$C_{1-4}$alkoxy, $OC(=O)R_7$, or $C(=O)R_7$; $C_{3-7}$ alkenyl unsubstituted or substituted optionally with OH, $NR_5R_6$, or $C_{1-4}$ alkoxy; $C_{3-7}$ alkynyl unsubstituted or substituted optionally with OH, $NR_5R_6$, or $C_{1-4}$ alkoxy; $C_{1-3}$ alkyl substituted with phenyl or $R_{10}$ either of which can be unsubstituted or substituted optionally with $C_1$-$C_3$alkyl, $C_1$-$C_3$halo alkyl, OH, $(CH_2)_nNR_5R_6$, halogen, $C_{1-4}$ alkoxy, $C_{1-4}$ haloalkoxy, $C(=O)R_7$, $S(=O)_mR_8$ or $SO_2NR_5R_6$, wherein m is 0–2 and n is 0–2; $C_{2-4}$ alkoxy substituted optionally with $NR_5R_6$, halogen, $C_{1-4}$ alkoxy, or $C(=O)R_7$; phenyl or $R_{10}$ either of which can be unsubstituted or substituted optionally with $C_1$-$C_3$alkyl, $C_1$-$C_3$halo alkyl, OH, $(CH_2)_nNR_5R_6$, halogen, $C_{1-4}$ alkoxy, $C_{1-4}$ haloalkoxy, $C(=O)R_7$, $S(=O)_mR_8$ or $SO_2NR_5R_6$, wherein m is 0–2 and n is 0–2; provided that $R_1$ and $R_2$ cannot both be H; or $R_1$ and $R_2$ can be joined to form a saturated ring of 5 or 6 atoms selected from O, S, C or N, such as, pyrrolidine, oxazolidine, thiomorpholine, thiomorpholine 1,1 dioxide, morpholine, piperazine, thiazolidine 1,1 dioxide, or tetrahydrooxazine, which can be unsubstituted or substituted optionally on carbon with OH, $NR_5R_6$, halogen, $C_{1-4}$ alkoxy, $C(=O)R_7$, $C_{1-6}$ alkyl, $C_{1-6}$ alkyl substituted optionally with OH, $NR_5R_6$, halogen, $C_{1-4}$ alkoxy, $C(=O)R_7$ or on nitrogen with $NR_5R_6$, $C_{1-4}$ alkoxy, $C(=O)R_7$, $C_{1-6}$ alkyl or $C_{2-6}$ alkyl substituted optionally with OH, $NR_5R_6$, halogen, $C_{1-4}$ alkoxy or $C(=O)R_7$.

$R_3$ is H; halogen; $C_{1-4}$ alkyl; $C_{1-8}$ alkoxy; $C_{1-8}$ alkylthiol; $C_{2-8}$ alkoxy substituted optionally with OH, $NR_5R_6$, halogen, $C_{1-4}$ alkoxy or $C(=O)R_7$; $C_{1-4}$ alkyl substituted optionally with $R_4$; or $R_1$ and $R_3$ can be joined together with carbon atoms to form a ring of from 5 to 7 members in which said carbon atoms can be unsubstituted or substituted optionally with $R_4$.

$R_4$ is OH; $C_{1-4}$ alkyl unsubstituted or substituted optionally with OH, $NR_5R_6$, halogen, $C_{1-4}$ alkoxy or $C(=O)R_7$; $C_{1-4}$ alkoxy; $C_{2-4}$ alkoxy substituted optionally with OH, $NR_5R_6$, halogen, $C_{1-4}$ alkoxy or $C(=O)R_7$; $NR_5R_6$; phenyl or $R_{10}$ either of which can be unsubstituted or substituted optionally with OH, $(CH_2)_nNR_5R_6$, halogen, $C_{1-4}$ alkoxy, $C_{1-4}$ haloalkoxy, $C(=O)R_7$, $S(=O)_mR_8$ or $SO_2NR_5R_6$, wherein m is 0–2 and n is 0–2;

Provided that when G is SO$_2$ and R$_3$ is in the 4 position and is H or halogen then R$_1$ and R$_2$ are not H, C$_{1-6}$ alkyl substituted optionally with OH, C$_{1-6}$ alkoxy, C$_{2-6}$ alkoxycarbonyl, C$_{2-6}$ alkenyl, phenyl, phenoxy, pyridyl, tetrahydrofuryl, C$_{2-6}$ alkanoyl, C$_{2-6}$ alkenyl, nor are they joined to form a 5, 6 or 7 member ring, saturated or unsaturated, comprised of atoms selected optionally from C, O, S, N in which said nitrogen, when saturated, is substituted optionally with H or C alkyl or in which said carbon is substituted optionally with C alkyl, C$_{1-6}$ alkoxy or OH; and when R$_3$ is in the 5 position and is H, Cl, Br, or C$_{1-3}$ alkyl then neither R$_1$ nor R$_2$ can be H or C$_{1-4}$ alkyl; and when G is C(=O) and in the 5- position and R$_3$ is H, then R$_1$ and R$_2$ cannot both be CH$_3$;

R$_5$ & R$_6$ are the same or different and are H; C$_{1-4}$ alkyl; C$_{2-4}$ alkyl substituted optionally with OH, halogen, C$_{1-4}$ alkoxy or C(=O)R$_7$; C$_{1-4}$ alkoxy; C$_{2-4}$ alkoxy substituted optionally with OH, halogen, C$_{1-4}$ alkoxy or C(=O)R$_7$; C$_{3-7}$ alkenyl unsubstituted or substituted optionally with OH, NR$_5$R$_6$, or C$_{1-4}$ alkoxy; C$_{3-7}$ alkynyl unsubstituted or substituted optionally with OH, NR$_5$R$_6$, or C$_{1-4}$ alkoxy; C$_{1-2}$alkylC$_{3-5}$cycloalkyl; C(=O)R$_7$ or R$_5$ and R$_6$ can be joined to form a ring of 5 or 6 atoms selected from O, S, C or N, such as, pyrrolidine, oxazolidine, thiomorpholine, thiomorpholine 1,1 dioxide, morpholine, piperazine or thiazolidine 1,1-dioxide, which can be unsubstituted or substituted optionally on carbon with OH, (=O), halogen, C$_{1-4}$ alkoxy, C(=O)R$_7$, C$_{6-1}$ alkyl, C$_{1-6}$ alkyl substituted optionally with OH, halogen, C$_{1-4}$ alkoxy, C(=O)R$_7$ or on nitrogen with C$_{1-4}$ alkoxy, C(:O)R$_7$, S(=O)$_m$R$_8$, C$_{1-6}$ alkyl or C$_{2-6}$ alkyl substituted optionally with OH, halogen, C$_{1-4}$ alkoxy, C(:O)R$_7$ or on sulfur by (=O)$_m$, wherein m is 0–2.

R$_7$ is C$_{1-8}$ alkyl; C$_{1-8}$ alkyl substituted optionally with OH, NR$_5$R$_6$, halogen, C$_{1-4}$ alkoxy or C(=O)R$_9$; C$_{1-4}$ alkoxy; alkoxy substituted optionally with OH, NR$_5$R$_6$, halogen or C$_{1-4}$ alkoxy; NR$_5$R$_6$; or phenyl or R$_{10}$ either of which can be unsubstituted or substituted optionally with OH, halogen, C$_{1-3}$ alkyl, C$_{1-3}$ haloalkyl, (CH$_2$)$_n$NR$_5$R$_6$, S(=O)$_m$R$_8$ or SO$_2$NR$_5$R$_6$, wherein n is 0 or 1 and m is 0–2.

R$_8$ is C$_{2-4}$ alkyl; C$_{2-4}$ alkyl substituted optionally with OH, NR$_5$R$_6$, halogen, C$_{1-4}$ alkoxy or C(=O)R$_7$.

R$_9$ C$_{1-4}$ alkoxy; amino, C$_{1-3}$ alkylamino, or di-C$_{1-3}$ alkylamino; and R$_{10}$ is a monocyclic ring system of 5 or 6 atoms composed of C, N, O, and/or S, such as furan, thiophene, pyrrole, pyrazole, imidazole, triazole, tetrazole, oxazole, isoxazole, isothiazole, thiazole, thiadiazole, pyridine, pyrimidine, pyridazine, and pyrazine.

G is C(=O) or SO$_2$.

In the above definitions, the total number of carbon atoms in a substituent group is indicated by the C$_{i-j}$ prefix where i and j are numbers from 1 to 8 for example. This C$_{i-j}$ definition includes both the straight and branched chain isomers. For example, C$_{1-4}$ alkyl would designate methyl through the butyl isomers; and C$_{1-4}$ alkoxy would designate methoxy through the butoxy isomers.

The term "halogen," either alone or in compound words such as "haloalkyl," means fluorine, chlorine, bromine or iodine Further, when used in compound words such as "haloalkyl," said alkyl may be partially or fully substituted with halogen atoms, which may be the same or different.

Structure I includes isomers, wherein R$_3$ and GNR$_1$R$_2$ are attached to the 4 and 5 position respectively or R$_3$ is attached to the 5 position and GNR$_1$R$_2$ is attached to the 4 position. Many of the novel compounds of Structure I possess one or more chiral centers and this invention includes all enantiomers, diastereomers and mixtures thereof.

In addition to the following teaching, U.S. Pat. Nos. 5,153,192 and U.S. Pat. No. 5,240,923, the parents of this case which are commonly assigned, are incorporated herein by reference, particularly for their synthesis teaching and their many specific examples.

Compounds of the present invention can be prepared using a variety of procedures, a number of which are described below.

Many of the novel compounds of Structure I can be prepared from 5-sulfamoyl-thiophene-2-sulfonyl chlorides or 3-substituted 5-sulfamoyl-thiophene-2-sulfonyl chlorides, or where it is particularly advantageous for subsequent reactions in a specific preparation that the sulfonamide group be protected, 3-substituted 5-(N-t-butylsulfamoyl)-thiophene-2-sulfonyl chlorides can be used. These thiophene-2-sulfonyl chlorides can be readily prepared by a variety of procedures known in the art, for example see Gronowitz et al in *Thiophene and its Derivatives*, Vol. 44, Pt. 3, p135. The preparative sequence for novel compounds of Structure I using a protected sulfonamide is illustrated in Equation 1. In general, N-t-butyl-thiophene-2-sulfonamides can be selectively metallated at C5 using a strong organometallic base such as n-butyllithium, subsequent condensation with sulfur dioxide gas produces the intermediate lithium sulfinate salts (Equation 1a). The intermediate sulfinate salt can be readily converted to the corresponding sulfonyl chloride with an appropriate chlorinating agent such as N-chlorosuccinimide; amination of the sulfonyl chloride with a primary alkylamine, primary arylamine, or secondary alkylamine, bearing the desired R$_1$ and R$_2$ substituents, provides, following deprotection, the novel compounds of Structure I (Equation 1b).

In many cases it is more advantageous initially to prepare simplified primary or secondary sulfonamides as described above, but then append the more complex R$_1$ or R$_2$ substituents using standard alkylation reactions (Equation 1c). This sequence can furnish directly certain novel compounds of Structure I; however, subsequent modification of the substituents R$_1$, R$_2$, and R$_3$ can furnish yet other novel compounds of Structure I including novel fused bicyclic compounds; all of which can be prepared using methods known to one skilled in the art. Primary sulfonamides can be prepared from the corresponding sulfonyl chlorides by amination with ammonia or directly from the lithium sulfinate salts using hydroxylamine-O-sulfonic acid (HOSA) (Equation 1d). Equation 1

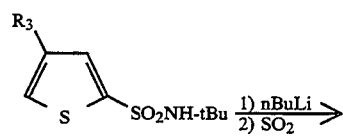

a)

-continued

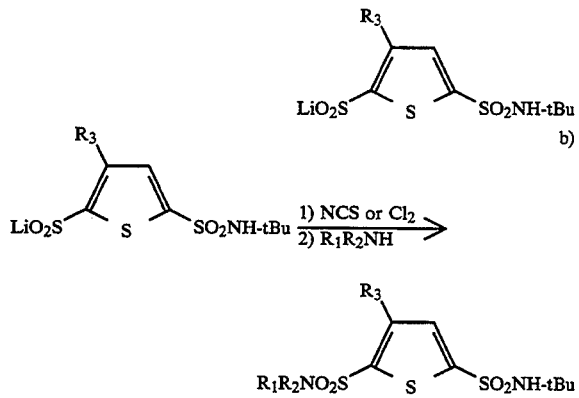

Equation 1 (continued)

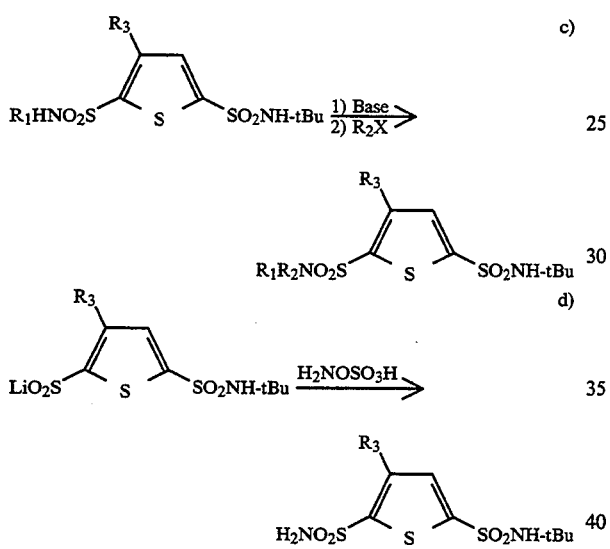

Many of the compounds of Structure I can be prepared using the procedures shown below in Equation 2 or other methods known in the art. Chlorosulfonation of thiophene-2-sulfonamides produces the 4-sulfonyl chlorides (Equation 2a). These intermediate sulfonyl chlorides can be converted to the novel compounds of Structure I using procedures (Equations 2b and 2c) analogous to those described for Equation 1.

Equation 2

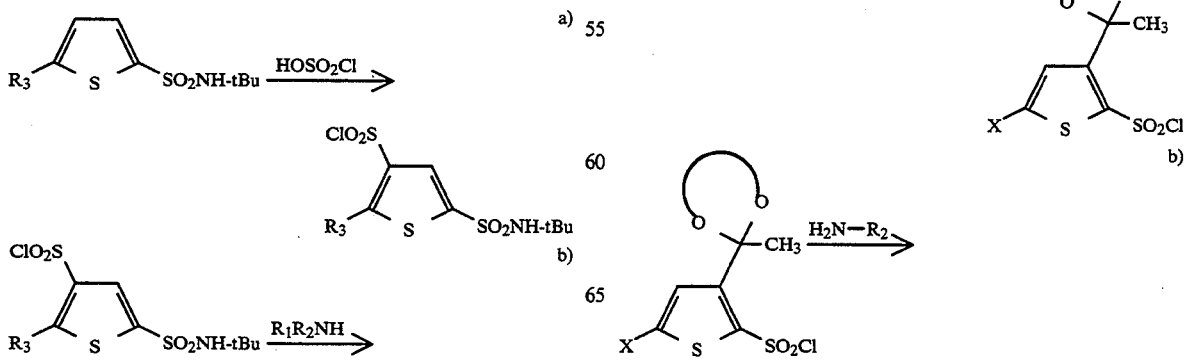

-continued

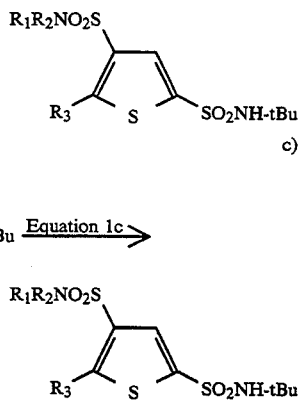

Novel compounds of Structure I wherein $R_1$ and $R_3$ are joined in a manner so as to provide fused bicyclic compounds, such as 3,4-dihydro-thieno-1,2-thiazine 1,1-dioxides, can be prepared from the appropriately substituted thiophenesulfonamides according to Equations 3–7. Thiophene ketals of Equation 3a, where X is H or halogen, can be readily prepared by standard methods well known to one skilled in the art from commercially available ketones. Treatment of these ketals by the methods of Equations 1a and 1b above provide the intermediate sulfonyl chloride. The sulfonyl chloride can be reacted with either ammonia to give the primary sulfonamide, or with the desired alkylamine or arylamine to give a secondary sulfonamide (Equation 3b). Alternately, the primary sulfonamide can be prepared from the intermediate sulfinate salt with hydroxylamine-O-sulfonic acid.

Equation 3

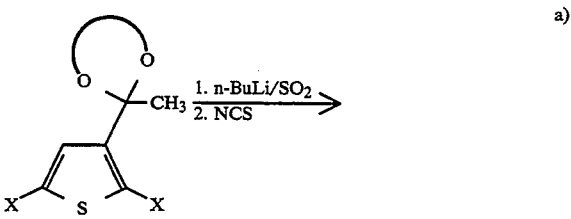

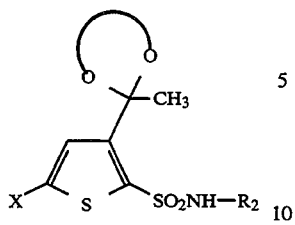

Conversion of these acyclic sulfonamides into the desired thienothiazine compounds can be accomplished using a variety of procedures well known in the art; e.g. acid hydrolysis of the ketal followed by bromination of the ketone and subsequent base catalyzed cyclization of the e-bromoketone (Equation 4).

Equation 4

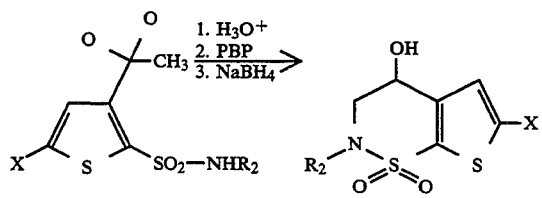

Certain desired bicyclic compounds of Structure I can be readily prepared by a sequence which involves initial alkylation with an appropriate alkyl halide in the presence of a suitable base (Equation 5a) followed by introduction of the sulfamoyl group by procedures analogous to Equations 1a–d, that is metallation of the alkylated product of Equation 4 with a strong organometallic base such as n-butyllithium, followed by treatment with sulfur dioxide to give the intermediate sulfinate salt which is aminated, e.g. by reaction with hydroxylamine-O-sulfonic acid (Equation 5b). Treatment of this intermediate with an appropriate alkyl nitrile in the presence of sulfuric acid provides an amide which upon reduction gives the desired amine [Equation 5c; R' is lower alkyl ($C_{1-4}$)].

Equation 5

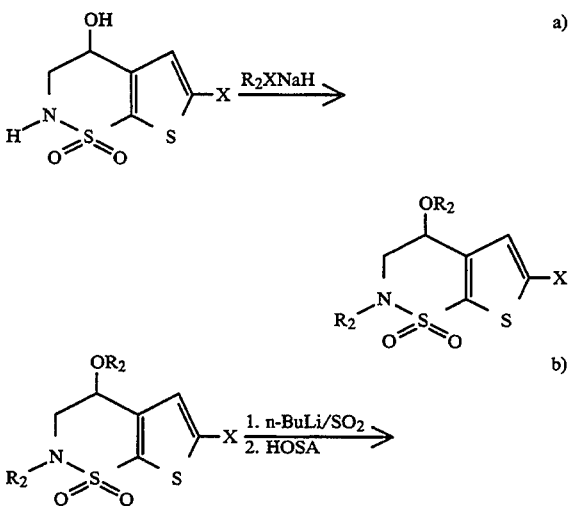

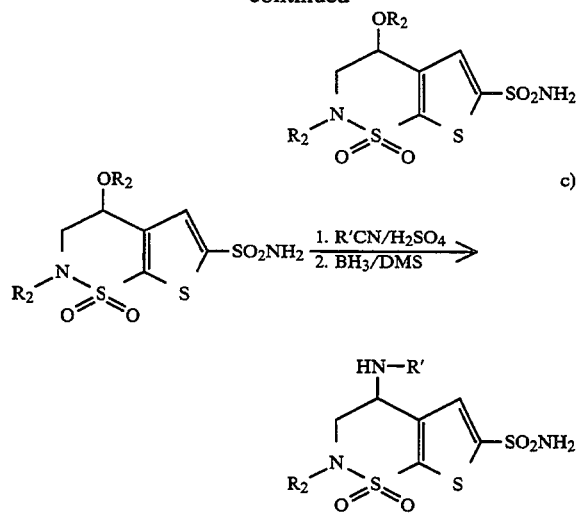

Yet other desirable compounds of Structure I are better prepared according to Equation 6 where the cyclic intermediate from Equation 4 is sulfamoylated (see Equation 5b) at position six (Equation 6a) followed by conversion of the hydroxyl group to a sulfonate ester (e.g. R" is p-toluyl or methyl) and reaction of this intermediate with the desired alkylamine (Equation 6b).

Equation 6

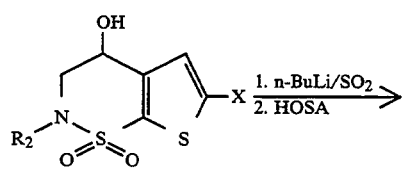

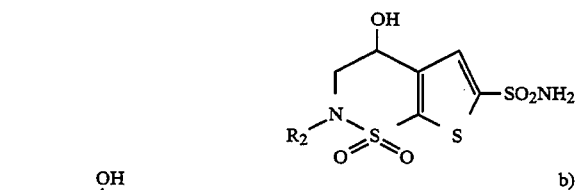

Still other desirable compounds of Structure I can be prepared (Equation 7) from an appropriate thienylethanol; these intermediate alcohols can be readily prepared by procedures well known in the art, e.g. reaction of thienyl-3-acetaldehyde with an appropriate Grignard reagent. Sulfamoylation of such alcohols by the procedures described in Equations 1a and 1d provide exclusively the desired thiophene-2-sulfonamide intermediates of Equation 7a. Cyclization to the desired bicyclic thienothiazine can be accomplished by procedures known in the art, but preferably cyclization is accomplished using conditions of the Mitsunobu reaction, diethyl azodicarboxylate-triphenylphosphine, or by displacement of a sulfonate ester under basic conditions (Equation 7b). The requisite $R_2$ group can be introduced using standard alkylation conditions (Equation 7c) and introduction of the primary sulfonamide can be accomplished by procedures similar to those already described in Equations 1a, 1b, and 1d (Equation 7d).

presence of a suitable activating agent such as dicyclohexylcarbodiimide, provides the primary or secondary thiophene-2-carboxamides, respectively (Equation 8a). Deprotection of the amides followed by bromination provides the α-bromoketones which can be readily cyclized under basic conditions (8b). Introduction of the desirable primary sulfonamide group can be accomplished in a manner analogous to that previously described in Equations 1a, 1b, and 1d. The alcohols can be transformed to amines if desired by initial conversion to an aryl or alkyl sulfonate ester and subsequent treatment with the desired amine (Equation 8c).

Equation 7

Equation 8

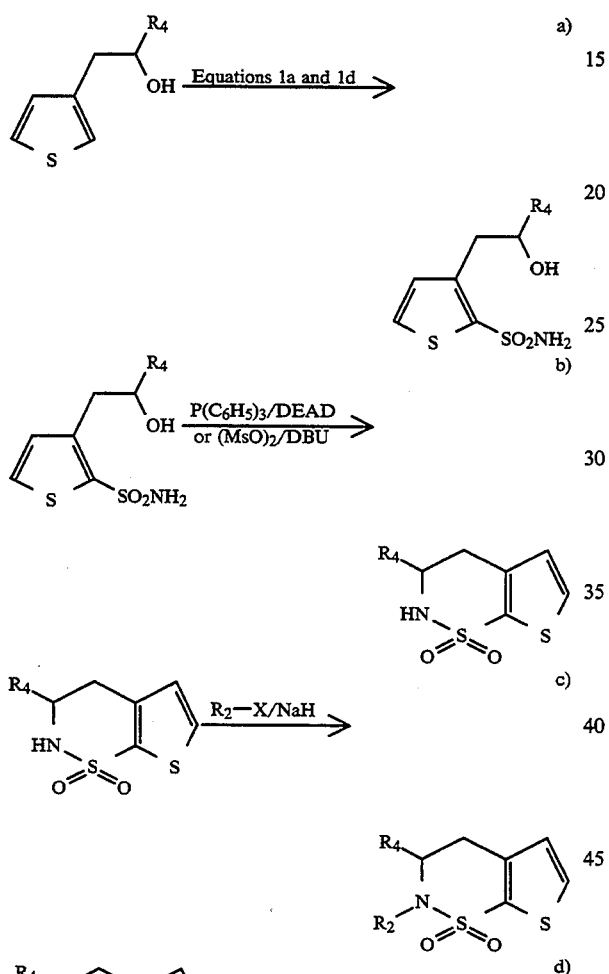

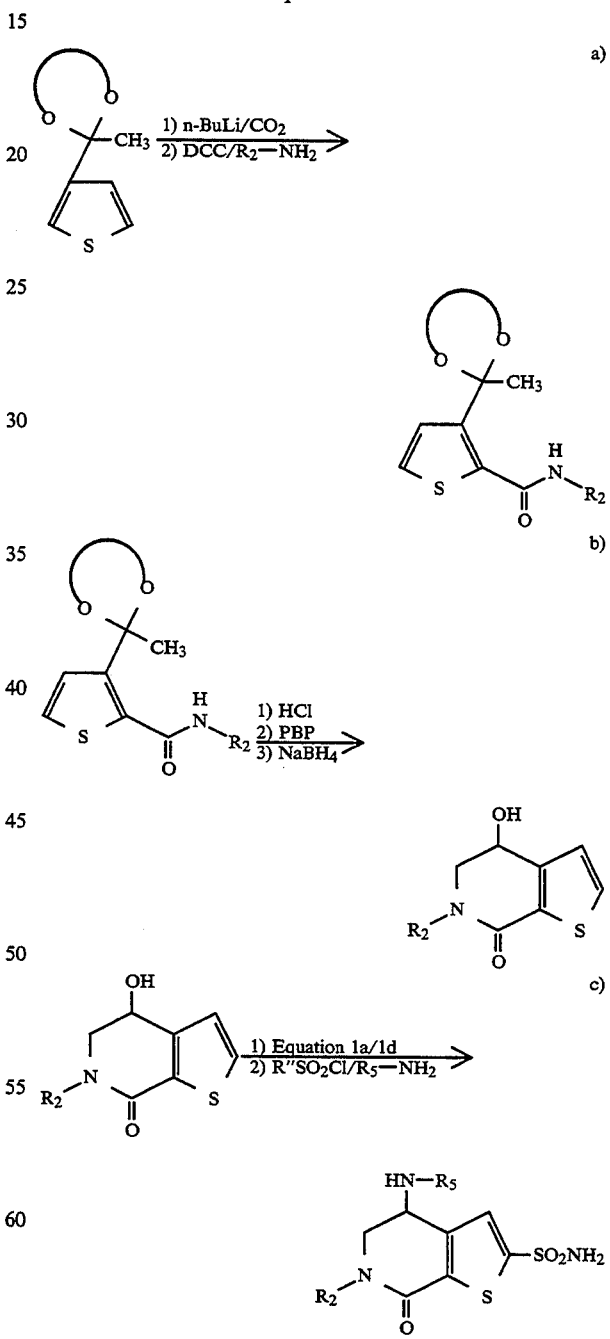

Yet other fused bicyclic compounds of Structure I, such as tetrahydrothieno[2,3-b]pyridine-2-sulfonamides, can be prepared in much the same manner as already described in Equations 2–6. Thiophene ketals (see Equation 3a) are readily metallated by strong organometallic bases and upon subsequent reaction with carbon dioxide provide the lithium carboxylates which upon coupling with ammonia or a desirable amine in the Alternately, such compounds can be prepared by the procedure shown in Equation 9. Alkylation of 4,5,6,7-tetrahydro-4-(trifluoroacetamido)-7-oxo-thieno[2,3- b]pyridine [Heterocycles, 27, 1637 (1988)] with the requisite $R_2$ group using standard alkylation procedures followed by hydrolysis of the amide provides the primary amine as shown in Equation 9a. This intermediate primary amine can be selectively transformed to more desirable secondary amines using well known methods of reductive amination, that is treatment with the desired aldehyde and a suitable reducing agent, or reductive alkylation, that is reaction with the requisite carboxylic acid and a suitable reducing agent [Equation 9b; G is H or loweralkyl ($C_{1-4}$)]. Introduction of the primary sulfonamide can be accomplished as previously described in Equations 1a, 1b, and 1d, but preferably using t-butyllithium as the base (Equation 9c).

Equation 9

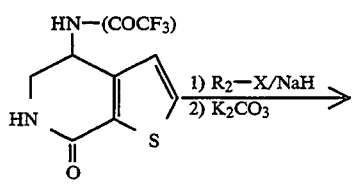

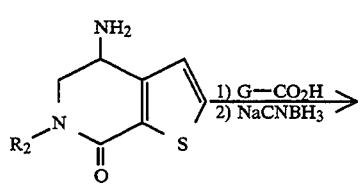

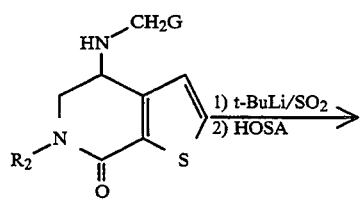

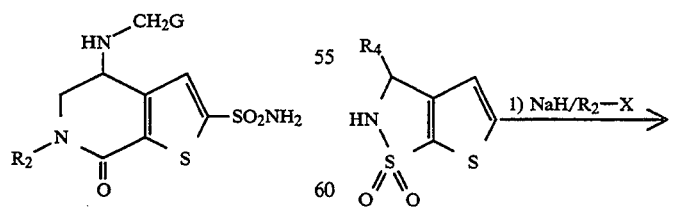

Certain cyclic compounds of Structure I, such as the 2,3-dihydrothienoisothiazoles, can be obtained through the modification of an existing cyclic compound (Equation 10). The metallated ketals of Equation 3 can be readily converted to the desired intermediate mercaptoketones as shown in Equation 10a, and the oxime 0-esters of such compounds can be cyclized according to Equation 5b. Oxidation and subsequent reduction of the thienoisothiazole by procedures well known in the art provides the intermediate cyclic sulfonamides shown in Equation 10c. These cyclic sulfonamides can be substituted on nitrogen utilizing standard alkylation procedures such as demonstrated by Equation 10d. Incorporation of the primary sulfonamide into position five of these examples of Structure I can be accomplished under the basic conditions demonstrated by Equations 1a-d. Equation 10

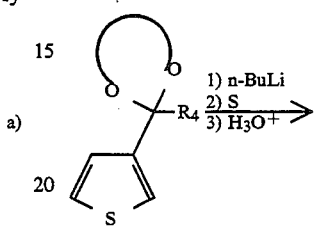

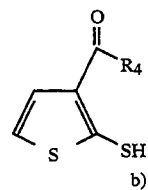

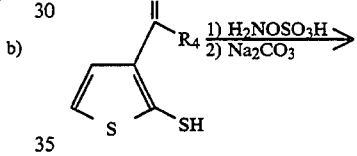

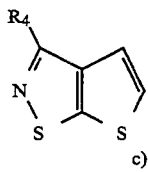

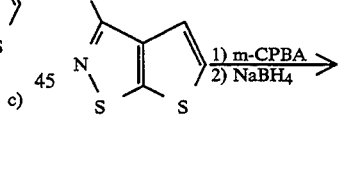

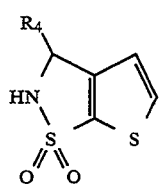

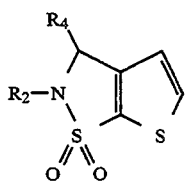

-continued

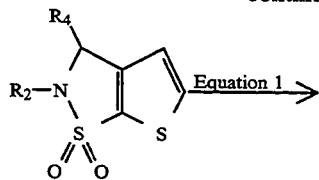

Equation 1 →

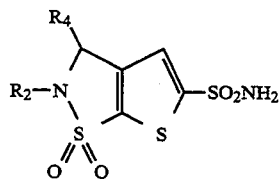

Yet other cyclic compounds of Structure I, such as tetrahydrothienothiazepines, can be prepared from substituted thiophenesulfonamides according to Equation 11. Thiophene acetals can be metallated in the two position with strong metallic bases in a manner similar to that described in Equation 3a for thiophene ketals. These intermediates can be further converted to the thiophene-2-sulfonamides desired for Equation 11a in a manner similar to that described for thiophene ketals by Equations 3a and 1d. Thiophene acetals can be readily converted to the corresponding aldehydes by acid hydrolysis, and reaction of these aldehydes with an olefinic Grignard reagent can provide the olefin intermediates of Equation 11a. The allylic alcohols from Equation 11a can be oxidized to intermediate ketones by a variety of procedures well known to the art, and these ketones can be cyclized upon treatment under basic conditions, such as sodium carbonate, to the cyclic sulfonamides (Equation 11b). The requisite $R_1$ group can be appended by using standard alkylation reactions (Equation 11c) and these intermediates can be reduced to the requisite alcohols with a suitable reagent, such as sodium borohydride. The alcohols can be transformed to amines by initial conversion to an alkyl or aryl sulfonic acid ester, and subsequent treatment of this intermediate with the desired primary or secondary amine (Equation 11d). Introduction of the primary sulfonamide functionality into the tetrahydrothienothiazepines can be accomplished by procedures similar to those already described in Equations 1a, 1b, and 1d (Equation 11e).

Equation 11

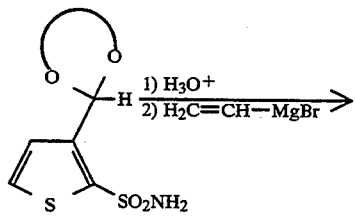 a)

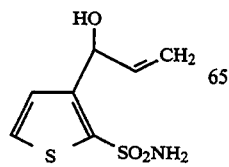

-continued

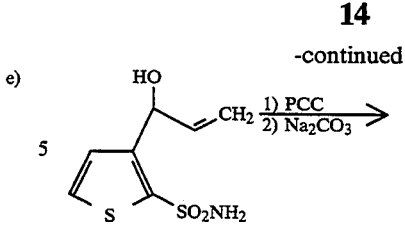 b)

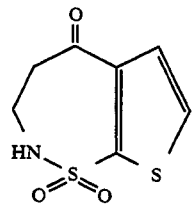

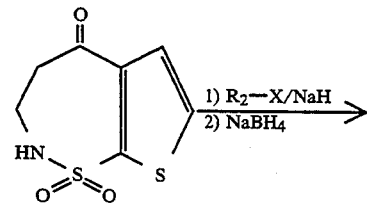 c)

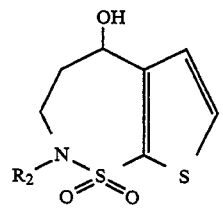

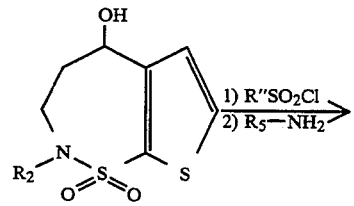 d)

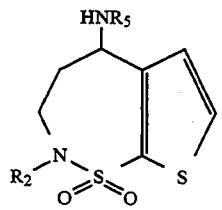

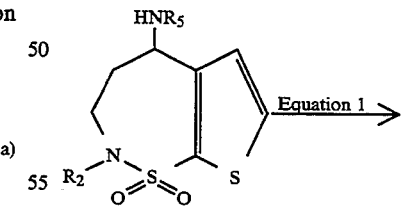 Equation 1 → e)

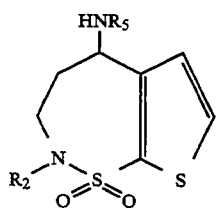

Thienothiazines isomeric to those described in Equations 4–7 can be prepared using a similar route starting from 2,5-dichlorothiophene as shown in Equation 12.

Chlorosulfonation of this starting material followed by amination using methods similar to those described in Equation 2 will provide the desired thiophene-3-sulfonamide (Equation 12a). Subsequent treatment of this intermediate with n-butyllithium at low temperature followed by quenching with acetic anhydride will give rise to the ketone of Equation 12b. This key intermediate can then be converted into the desired novel compounds of Structure I using substantially the same general methods described in Equations 4-6.

Equation 12

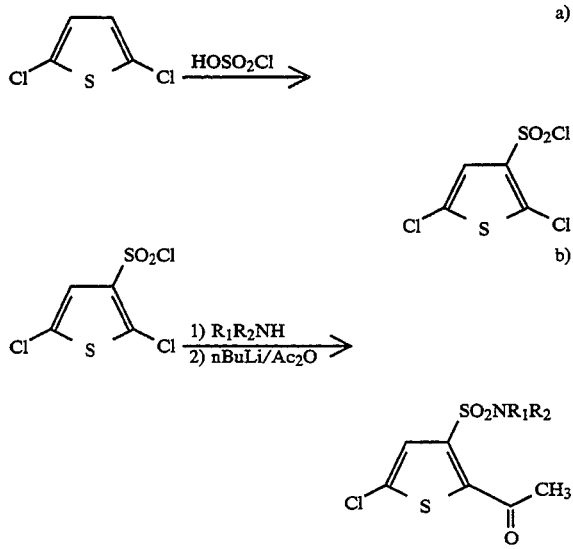

Still other desirable compounds of Structure I, such as 5-sulfamoyl-thiophene-2-carboxamides, can be prepared according to Equation 13. Treatment of the readily prepared 5-bromo-thiophene-2-sulfonamides under palladium mediated amidation reaction conditions [see for example *J. Org. Chem.*, 39, 3327 (1974)] in the presence of the desired amine component provides the novel compounds of Structure I. Alternately, 5-bromo-thiophene-2-sulfonamides can be initially protected, such as with the formamidine group, followed by treatment with a strong organometallic base, such as n-butyllithium or LDA, and carbon dioxide to give the intermediate carboxylic acid. Treatment of this intermediate acid with an activiating agent, such as dicyclohexylcarbodiimide or triphenylphosphine triflate, followed by reaction with the desired amine component provides, following deprotection, the desired compounds of Structure I.

Equation 13

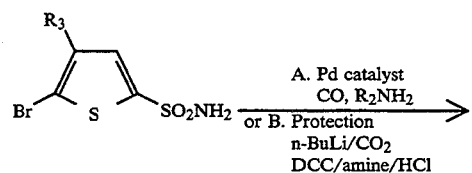

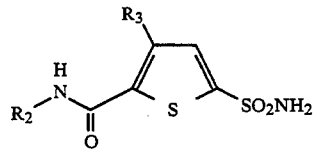

The compounds of Structure I can be incorporated into various types of ophthalmic formulations for delivery to the eye. These compounds may be combined with ophthalmologically acceptable preservatives, surfactants, viscosity enhancers, penetration enhancers, buffers, sodium chloride and water to form an aqueous, sterile ophthalmic suspensions or solutions. In order to prepare sterile ophthalmic ointment formulations, the active ingredient is combined with a preservative in an appropriate vehicle, such as, mineral oil, liquid lanolin, or white petrolatum. Sterile ophthalmic gel formulations may be prepared by suspending the active ingredient in a hydrophilic base prepared from the combination of, for example, carbopol-940 or the like according to the published formulations for analogous ophthalmic preparations; preservatives and tonicity agents can be incorporated. Ophthalmic solution formulations may be prepared by dissolving the active ingredient in a physiologically acceptable isotonic aqueous buffer. Further, the ophthalmic solution may include an ophthalmologically acceptable surfactant to assist in dissolving the active ingredient. Furthermore, the ophthalmic solution may contain a thickener such as hydroxymethylcellulose, hydroxyethylcellulose, hydroxypropylmethylcellulose, methylcellulose, polyvinylpyrrolidone, or the like to improve the retention of the medicament in the conjunctival sac.

The compounds are preferably formulated as topical ophthalmic suspensions or solutions, with pH of about 4.5 to 7.8. The compounds will normally be contained in these formulations in an amount of 0.1% to 10% by weight, but preferably in an amount of 0.25% to 5.0% by weight. Thus, for topical presentation 1 to 3 drops of these formulations would be delivered to the surface of the eye 1 to 4 times a day according to the routine discretion of a skilled clinician.

The following examples, which are in no way limiting, illustrate the preparation of selected examples of the novel compounds of Structure I. The compounds set forth in Examples 1, 4-4, 4-5, 4-8, 4-9, 5-2, 5-4, 7, and 8 represent the preferred thiophene sulfonamides of this invention. The compounds represented i n Examples 1, 7, and 8 are most preferred.

Example 1

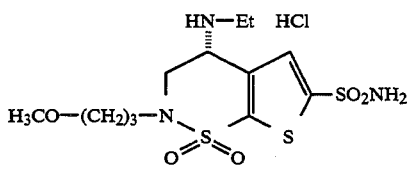

(+)-4-Ethylamino-3,4-dihydro-2-(3-methoxy)propyl-2H-thieno[3,2-e]-1,2-thiazine-6-sulfonamide-1,1-dioxide hydrochloride

Step A:
3-(2,5,5-Trimethyl-1,3-dioxane-2-yl)-2-thiophenesulfonamide

To a solution of 3-(2,5,5-Trimethyl-1,3-dioxane-2-yl)thiophene (2.5 g, 11.7 mmol) in hexane (30 mL) cooled to 0° C. was added via syringe n-butyllithium in hexane (2.5M, 10.3 mL, 25.7 mmol) over 5 min. The mixture was stirred at 0° C. for 20 min, the ice bath was removed and the stirring was continued for 30 min. At this time a white precipitate formed. The mixture was cooled to −60° C. and THF (20 mL) was added. Sulfur dioxide was then passed through the surface of the mixture for 30 min. The mixture was warmed to ambient temperature and stirred for an additional 15 min. The volatiles were evaporated and to the residue was added water (50 mL) and sodium acetate trihydrate (9.55 g, 70.2 mmol). The solution was cooled on an ice bath and hydroxylamine-O-sulfonic acid (4.62 g, 40.9 mmol) was added. The mixture was stirred at ambient temperature for 1 h, extracted with ethyl acetate (3×100 mL) and the combined extracts were washed with a sodium bicarbonate solution, brine and dried over molecular sieves. Evaporation to dryness gave a viscous liquid (4.93 g), which was chromatographed (silica, eluting with 33% ethyl acetate-hexane) to give a solid (2.47 g, 72%): mp 200°–202° C.

Step B: 3-Acetyl-2-thiophenesulfonamide

A mixture of the compound from Step A (9.45 g, 32.5 mmol) and 1N HCl (100 mL) in THF (100 mL) was heated at reflux for 1 h. The THF was evaporated and the aqueous solution was made basic by the addition of sodium bicarbonate. The mixture was cooled using an ice bath and the precipatiate was filtered, washed with cold water and dried in vacuo to give 5.83 g (88%) of a solid: mp 193°–196° C.

Step C:
3,4-Dihydro-4-hydroxy-2H-thieno[3,2-e]-2-thiazine 1,1-dioxide

The product from Step B (5.73 g, 28.0 mmol) was dissolved in hot THF (200 mL). The solution was cooled to 10° C. and pyridinium bromide perbromide (10.73 g, 33.5 mmol) was added. The mixture was allowed to stir at ambient temperature for 1 h. The volatiles were evaporated and the residue was mixed with water. The precipitate was filtered, washed with cold water and dried in vacuo overnight to give 7.77 g of a solid. A portion of this solid (3.49 g, 12.3 mmol) was suspended in ethanol (100 mL) and treated with sodium borohydride (266 mg, 7.04 mmol). The suspension turned clear after 10 min and was heated at reflux for 1 h. The ethanol was evaporated and the residue was extracted with ethyl acetate, washed with brine and evaporated to give the product (1.80 g, 71%): mp 138°–140° C.

Step D:
2-(3-Bromo)propyl-3,4-dihydro-4-hydroxy-2H-thieno[3,2-e]-1,2-thiazine The product from Step C (8.0 g, 39.0 mmol) was dissolved in anhydrous DMF (100 mL), cooled to −20° C. and sodium hydride (1.87 g, 46.8 mmol) was added. After stirring for five minutes, 1,3-dibromopropane (20 mL, 19.5 mmol) was added and the reaction mixture stirred for 3 hr at 0° C. The reaction mixture was diluted with ice water (100 mL) and this solution was extracted with ethyl acetate (3×30 mL). The combined extracts were washed with brine (30 mL), dried (MgSO4), and evaporated to give a crude product which was purified by column chromatography [silica; CH3OH/CH2Cl2(20:1)] to provide the desired product (10.1 g, 79%) as a syrup.

Step E:
2-(3-Bromo)propyl-4-(1-ethoxy)ethoxy-3,4-dihydro-2H-thieno-[3,2-e]-1,2-thiazine The product from Step D (10.1 g, 30.1 mmol) and p-toluenesulfonic acid (1.1g) were dissolved in THF (100 mL) and cooled to −20° C. at which point ethylvinyl ether (5.8 mL, 60.2 mmol) was added. This mixture was allowed to warm to 0° C. and kept at this temperature for 1.5 hr followed by dilution with cold ethyl acetate (200 mL). The organic layer was separated, washed with saturated sodium bicarbonate (3×50 mL) and brine (50 mL), dried (MgSO4), and evaporated to provide 9.5 g (79%) of crude product which was used in the next step without further purification.

Step F:
4-(1-Ethoxy)ethoxy-3,4-Dihydro-2-(3-methoxy)propyl-2H-thieno[3,2-e]-1,2-thiazine.

The product from Step E (9.5 g, 23.8 mmol) was dissolved in methanol (200 ml) and sodium methoxide (6.5 g, 119 mmol) was added; the mixture was heated at reflux temperature for 18 hr. Evaporation of the solvent gave the crude product which was dissolved in ethyl acetate (300 mL). This solution was washed with water (3×50 mL) and brine (3×35 mL), dried (MgSO4) and evaporated to provide the crude product which was purified by column chromatography [silica; CH3OH/CH2Cl2(20:1)] to give 6.5 g (78%) of product as a syrup.

Step G:
3,4-Dihydro-4-hydroxy-2-(3-methoxy)propyl-2H-thieno[3,2-e]-1,2-thiazine-6-sulfonamide-1,1-dioxide.

The product from Step F (6.5 g, 18.6 mmol) was dissolved in THF (40 mL), cooled to −78° C. and treated sequentially with n-butyllithium, sulfur dioxide, and hydroxylamine-O-sulfonic acid in a manner essentially identical to that described in Example 2, Step D to provide the desired crude product which, after purification by column chromatography, provided 4.1 g (62%) of an amber syrup.

Step H:
3,4-Dihydro-2-(3-methoxy)propyl-4-oxo-2H-thieno[3,2-e]-1,2-thiazine-6-sulfonamide-1,1-dioxide.

To a solution of the product from Step G (3.8 g, 10.7 mmol) in acetone (40 mL) at room temperature was added Jones reagent [9.7 mL (prepared by dissolving CrO3 (7 g) in H2O (50 mL) and adding H2SO4 (6.1 mL)]. This mixture was stirred at room temperature for one hour, diluted with ethyl acetate (200 mL) and washed with a 5% solution of sodium bisulfite (2×100 mL) and brine (2×50 mL), dried (MgSO4), and evaporated to a syrup which was purified by column chromatography [silica; CH3OH/CH2Cl2(20:1)] to give 2.7 g (70%) of the desired product: mp 115°–117° C.

Step I:
(S)-3,4-Dihydro-4-hydroxy-2-(3-methoxy)propyl-2H-thieno[3,2-e]-1,2-thiazine-6-sulfonamide-1,1-di oxide To a solution of the product of Step H (2.6 g, 7.34 mmol) in THF (30 mL) at −78° C. was added a solution of (+)-β-chlorodiisopinocampheylborane (11.8 g, 36.7 mmol) in THF (10 mL). The reaction mixture was allowed to warm to −20° C. and kept at this temperature for 4 days. Diethanolamine (4.2 mL, 44 mmol) was added to the reaction mixture and the solution stirred for 30 min, diluted with EtOAc (150 mL), washed with water (2×50 mL) and brine (2×50 mL), dried (MgSO4), and evaporated to a syrup which was purified by column chromatography [silica; CH3OH/CH2Cl2(20:1)] to give 2.4 g (92%) of the desired compound as a colorless foam.

Step J:
(+)-4-Ethylamino-3,4-dihydro-2-(3-methoxy)propyl-2H-thieno[3,2-e]-1,2-thiazine-6-sulfonamide-1,1-dioxide hydrochloride To a solution of the product from Step I (2.4 g, 6.74 mmol) and triethylamine (3.8 mL, 27 mmol) in anhydrous tetrahydrofuran (20 mL) cooled to −20° C. was added tosyl chloride (2.6 g, 13.5 mmol); this mixture was allowed to warm to room temperature and stirred for 18 hr. The reaction mixture was cooled to −60° C. and ethylamine (10 mL) was added and the mixture was again allowed to warm to room temperature. After 18 hr the reaction mixture was diluted with ethyl acetate (200 mL), washed with a saturated aqueous solution of sodium bicarbonate (3×50 mL), dried (MgSO4), and evaporated to give the crude product which was purified by column chromatography [silica; CH3OH/CH2Cl2(20:1)] to give 1.3 g (52%) of the desired amine. The free base was dissolved in ethanol (5 mL) and treated with a 2M solution of hydrochloric acid in ethanol (4 mL) at room temperature. Evaporation of the solvent provided a solid which was recrystallized from methanol: methylene chloride to give 950 mg (34%) of the desired product; mp 175°–177° C.; [α]$_D$+10.35° (C=1.00, H2O). Analysis. Calculated for C12H22ClN3O5S3: C, 34.32; H, 5.28; N, 10.00 Found: C, 34.26; H, 5.23; N, 9.92.

EXAMPLE 2

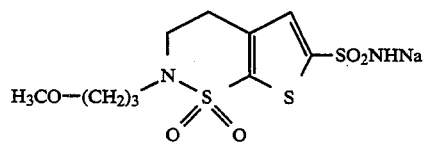

3,4-Dihydro-2-(3-methoxypropyl)-2H-thieno[3,2-e]-1,2-thiazine-6-sulfonamide-1,1-dioxide sodium salt

Step A:
3,4-Dihydro-4-hydroxy-2-(3-methoxypropyl)-2H-thieno[3,2-e]-1,2-thiazine- 1,1-dioxide The product from Example 1, Step C (2.0 g, 9.74 mmol) was added to a suspension of sodium hydride (0.4 g, 10.0 mmol, of a 60% suspension in mineral oil) in DMF (30 mL) and the mixture was stirred for 1 hr. then cooled to 20° C. 3-Bromopropyl methyl ether (1.5 g, 9.74 mmol) was added and the mixture was stirred overnight then quenched with water (200 mL), and extracted with ethyl acetate (4×30 mL). The extracts were combined, washed with water (100 mL), dried (MgSO4) and concentrated under reduced pressure which provided an oil which was purified by column chromatography (silica, gradient: hexane to ethyl acetate) to give 1.7 g (63%) of a clear oil which was not purified further.

Step B:
3,4-Dihydro-2-(3-methoxypropyl)-4-O-phenoxythiocarbonyl-2H-thieno[3,2-e]-1,2-thiazine 1,1-dioxide The product from Step A (1.68 g, 6.06 mmol) and DMAP (1.48 g, 12.11 mmol) were dissolved in 1,2-dichloroethane (16 mL) and cooled in an ice bath. Phenoxythiocarbonyl chloride (1.26 mL, 9.09 mmol) was added slowly and the reaction mixture was stirred at room temperature overnight, then quenched with water (40 mL). The mixture was extracted with dichloromethane (3×10 mL) and the extracts were combined, washed with saturated sodium chloride solution, dried (MgSO4) and concentrated under reduced pressure. The residue was purified by column chromatography (silica, gradient: hexane to 3:1 hexane/ethyl acetate) to give 1.75 g (70%) the desired product as an oil which was used in the next step.

Step C:
3,4-Dihydro-2-(3-methoxypropyl)-2H-thieno[3,2-e]-1,2-thiazine 1,1-dioxide The product from Step B (1.75 g, 4.23 mmol) and AIBN (100 mg) were mixed with dry benzene (12 mL) and degassed under nitrogen. The mixture was heated to reflux and tributyltin hydride (1.2 mL, 4.44 mmol) was added rapidly dropwise to maintain a gentle reflux. Heating was continued for 30 min and the reaction mixture was concentrated under reduced pressure. The residue was purified by column chromatography (silica, gradient: hexane to 3:1 hexane/ethyl acetate) to provide the desired product (1.06 g, 95%) as a clear oil.

Step D:
3,4-Dihydro-2-(3-methoxypropyl)-2H-thieno[3,2-e]-1,2-thiazine-6-sulfonamide 1,1-dioxide sodium salt The product form Step C (1.03 g, 3.94 mmol) was dissolved in dry THF (20 mL) and cooled (−65° C.) under nitrogen. n-Butyllithium (2.1 mL of a 2.1M solution in hexanes) was added dropwise and the mixture was stirred for 45 min, then excess sulfur dioxide was introduced into the flask until the solution tested acidic to moist litmus paper. The reaction mixture was concentrated under reduced pressure and the residue was dissolved in water (25 mL) and sodium acetate trihydrate (2.68 g, 19.7 mmol) then hydroxylamine-O-sulfonic acid (1.34 g, 11.8 mmol) were added and the mixture was stirred at room temperature for 16 hr followed by extraction with ethyl acetate (5×5 mL). The extracts were combined, washed with saturated sodium chloride solution, dried (MgSO4) and concentrated. The residue was purified by column chromatography (silica, gradient: 3:1 hexane/ethyl acetate to 7:3 methylene chloride/methanol) which gave the desired product (1.21 g, 69%) as an amber syrup which was converted to the sodium salt as follows: The residue was dissolved in 2N NaOH (1.78 mL, 3.56 mmol), then mixed with ethanol (1.8 mL) and cooled. Ethyl ether was added to the cloud point and the product precipitated from the solution. The solids were collected and dried to provide the desired product (0.94 g, 73%) as a white solid: mp 169°–170° C. Analysis: Calculated for $C_{10}H_{15}N_2O_5S_3Na\cdot 0.5\ H_2O$: C, 32.34; H, 4.34; N, 7.54. Found: C, 32.27; H, 4.19; N, 7.42.

By following the above general procedure but using instead 2-bromoethyl methyl ether or 4-bromobutyl methyl ether in Step A the following compounds were prepared.
1. 3,4-Dihydro-2-(2-methoxyethyl)-2H-thieno[3,2-e]-1,2-thiazine-6-sulfonamide 1,1-dioxide, mp 131°–132° C.;
2. 3,4-Dihydro-2-(3-methoxybutyl)-2H-thieno[3,2-e]-1,2-thiazine-6-sulfonamide 1,1-dioxide sodium salt, mp 244° C.

EXAMPLE 3

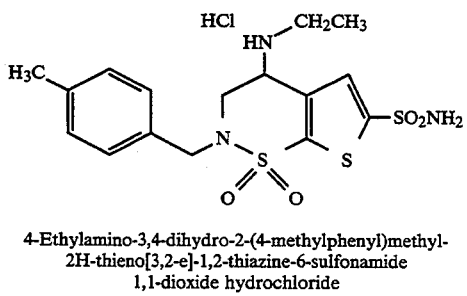

4-Ethylamino-3,4-dihydro-2-(4-methylphenyl)methyl-2H-thieno[3,2-e]-1,2-thiazine-6-sulfonamide 1,1-dioxide hydrochloride Step A: 3,4-Dihydro-4-hydroxy-N-(1,1-dimethyl)ethyl-2H-thieno[3,2-e]-1,2-thiazine-6-sulfonamide 1,1-dioxide To a solution of the product from Example 1, Step C (6.25 g, 30 mmol) in THF (40 mL) at 0° C. was added p-toluenesulfonic acid (200 mg) and ethyl vinyl ether (10.3 mL, 0.107 mol). The mixture was stirred for 6 hr at 0° C. followed by the addition of an aqueous solution of sodium bicarbonate (100 mL). The organic layer was separated and the aqueous layer was extracted with ethyl acetate (3×50 mL). The extracts were combined, washed with brine (30 mL), dried (MgSO4) and evaporated to give an oil which was purified by column chromatography (silica; 30% ethyl acetate/hexane) to give the desired protected intermediate product (10.1 g, 99%). To a solution of this material (9.6 g, 28 mmol) in THF (60 mL) was added a solution of n-butyllithium in pentane (20.6 mL of a 2.0M solution) at −78° C. over a period of 20 minutes. After stirring this solution for 45 min, a stream of sulfur dioxide gas was passed over the surface of the solution (20 min). The reaction mixture was allowed to warm to room temperature and stirred at this temperature for 2 hr. The solvent was evaporated to give a residue which was dissolved in methylene chloride (200 mL), cooled to 0° C., and N-chlorosuccinamide (7.4 g, 55 mmol) was added in portions. After one hour the reaction mixture was allowed to warm to room temperature; stirring continued for two more hours, at which point the methylene chloride was removed by evaporation and the residue dissolved in THF (100 mL). This solution was cooled (0° C.) and a solution of t-butylamine (7.8 mL, 75 mmol) in THF (50 mL) was added dropwise followed by stirring for 8 hr at room temperature. After removal of excess amine by evaporation, 2N HCl (10 mL) was added and the reaction mixture stirred at room temperature for 8 hr. Water (50 mL) was added and the organic layer separated. The aqueous layer was extracted with ethyl acetate (3×100 mL) and the combined organic layers were washed with brine (30 mL), dried (MgSO4), and evaporated to provide crude product which was purified by column chromatography (silica; 5% methanol/methylene chloride) to give the desired product as a yellow syrup (7.3 g, 72%).

Step B: 3,4-Dihydro-4-hydroxy-N-(1,1-dimethyl)ethyl-2-(4-methylphenyl)methyl-2H-thieno[3,2-e]-1,2-thiazine-6-sulfonamide 1,1-dioxide The product from Step A (4.0 g, 12 mmol) was dissolved in anhydrous DMF (40 mL) and added to a suspension of sodium hydride (0.58 g of a 60% dispersion in mineral oil, 14.4 mmol) in anhydrous DMF (30 mL) at 0° C.; this mixture was stirred at 0° C. for 3 hr. α-Chloro-p-xylene (2.2 mL, 24 mmol) was added and the solution was allowed to warm to room temperature, stirring continued at this temperature for 72 hr. The DMF was evaporated and the residue was suspended in water (60 mL); this mixture was extracted with ethyl acetate (4×50 mL) and the combined extracts were dried (Na2SO4), filtered, and evaporated to give a brown solid (5.12 g, 99%) which was not purified further.

Step C: 4-Ethyl amino-3,4-dihydro-N-(1,1-dimethyl)ethyl-2-(4-methylphenyl)methyl-2H-thieno[3,2-e]-1,2-thiazine-6-sulfonamide 1,1-dioxide The product from Step B (2,5 g, 7.3 mmol) was dissolved in anhydrous THF (960 mL) under nitrogen. The solution was cooled to 0° C. and p-toluenesulfonyl chloride (2.21 g, 12 mmol) and triethylamine (3.23 mL, 0.23 mol) were added. The mixture was stirred for 16 hr at 0° C. and then cooled to −60° C. Ethylamine (50 mL, 0.76 mol) was condensed into the reaction mixture and the solution was allowed to warm to room temperature and stirred for 72 hr. The solvent was evaporated and the residue was suspended in water (100 mL). The aqueous mixture was extracted with ethyl acetate (5×100 mL) and the combined extracts were dried (Na2SO4), filtered, and evaporated to an oil which was purified by column chromatography (silica, gradient: 70% hexane/ethyl acetate to 50% hexane/ethyl acetate) to give a brown oil (1.33 g, 51%).

Step D: 4-Ethylamino-3,4-dihydro-2-(4-methylphenyl)methyl-2H-thieno[3,2-e]-1,2-thiazine-6-sulfonamide 1,1-dioxide hydrochloride The product from Step C (1.3 g, 3 mmol) was dissolved in trifluoroacetic acid (15 mL) and stirred at room temperature for 16 hr. The trifluoroacetic acid was removed by evaporation, ethyl acetate (30 mL) was added and it was also removed by evaporation to give a residue which was suspended in water (30 mL). This mixture was extracted with ethyl acetate (3×30 mL) and the combined extracts were dried (Na2SO4), and evaporated to an oil which was purified by column chromatography (silica, 80% ethyl acetate/hexane) to give a white solid (400 mg). This material was dissolved in ethanol (25 mL) and treated with an excess of ethanolic hydrogen chloride for 2 hr; evaporation of the ethanol gave a white solid. This solid was dissolved in water (40 mL), evaporated, and dried to give the desired product (0.41 g, 32%) as a white solid: mp 207°–210° C. Analysis: Calculated for $C_{16}H_{22}ClN_3O_4S_3\cdot 1.5\ H_2O$: C, 40.10; H, 5.26; N, 8.80. Found: C, 40.35; H, 4.75; N, 8.65.

By following the above general procedure but using the appropriate arylalkyl halide in Step B and either n-propylamine or ethylamine in Step C the following compounds were prepared:
1. 3,4-Dihydro-2-(3-phenylpropyl )-4-propylamino-2H-thieno[3,2-e]-1,2-thiazine-6-sulfonamide 1,1-dioxide hydrochloride, mp 124°-127° C.
2. 3,4-Dihydro-2-(4-phenylbutyl )-4-propylamino-2H-thieno[3,2-e]-1,2-thiazine-6-sulfonamide 1,1-dioxide hydrochloride, mp 120°-125° C.
3. 4-Ethylamino-3,4-dihydro-2-(2-thienyl )methyl-2H-thieno[3,2-e]-1,2-thiazine-6-sulfonamide 1,1-dioxide hydrochloride, mp 182°-184° C.

EXAMPLE 4

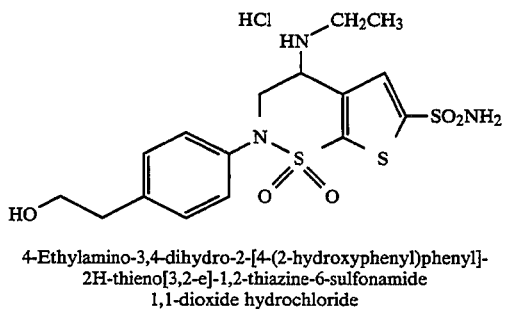

4-Ethylamino-3,4-dihydro-2-[4-(2-hydroxyphenyl)phenyl]-2H-thieno[3,2-e]-1,2-thiazine-6-sulfonamide
1,1-dioxide hydrochloride

Step A: 3-Acetyl-2-(phenylmethyl )thio-5-chlorothiophene

A mixture consisting of thiourea (858.4 g, 11.28 mol), benzyl bromide (1,930 g, 11.28 mol), THF (9000 ml), and water (3000 ml) was heated at reflux temperature for 2 hr followed by cooling to 50° C. To this solution was added 3-acetyl-2,5-dichlorothiophene (2000 g, 10.25 mol) and an aqueous solution of sodium hydroxide (2,200 g of 50% NaOH diluted to 3000 ml); this mixture was heated at reflux temperature for 4 hr, cooled to room temperature, and the two layers separated. The organic layer was diluted with ethyl acetate (6000 ml) and washed with water (3×2000 ml) and saturated aqueous sodium chloride, dried (MgSO4), and the solvent evaporated to give a residue which was triturated with hexane. This solid was collected by filtration and dried to give the desired product (2,550 g, 88%): mp 86°-88° C.

Step B: 3-Acetyl -5-chloro-N-[4-(2-hydroxyethyl)phenyl]-thiophene-2-sulfonamide The product from Step A (15 g, 0.058 mol) was dissolved in glacial acetic acid (150 mL), water (15 mL) was added and the solution cooled to 3° C. Chlorine gas was slowly passed through the solution until the temperature reached 15° C. at which point the mixture was cooled to 5° C. before the addition of chlorine was continued; this sequence was repeated four times. The reaction mixture was poured into ice water (400 mL) and extracted with methylene chloride (3×200 mL). The combined extracts were washed with cold saturated aqueous NaHCO3 (2×250 mL), dried (MgSO4), and evaporated. The sulfonyl chloride obtained from this procedure was dissolved in THF (50 mL) and added to a solution of 4-(hydroxyethyl)aniline (16 g, 0.116 mol) in THF (100 mL); this mixture was stirred for 2 days followed by evaporation of the solvent. The residue was suspended in 1M HCl and extracted with methylene chloride (2×100 mL). The combined extracts were washed with 1N HCl and then dried (MgSO4), filtered, and evaporated to a syrup which was purified by column chromatography (silica, gradient: 3% to 5% ethanol/methylene chloride) to provide a yellow solid (11.6 g, 56%): mp 112°-116° C.

Step C: 6-Chloro-3,4-dihydro-2-[4-[2-(t-butyldiphenylsiloxy)ethyl]phenyl]-4-hydroxy-2H-thieno[3,2-e]-1,2-thiazine 1,1-dioxide The product from Step B (11.5 g, 0.032 mol) was added to DMF (100 mL) containing imidazole (5.44 g, 0.08 mol) and t-butyldiphenylsilyl chloride (9.34 mL, 0.035 mol) and stirred at room temperature for 18 hr. The reaction mixture was evaporated to dryness and the residue was suspended in methylene chloride and filtered. The filtrate was concentrated and chromatographed (silica, methylene chloride) to provide a solid which was dissolved in THF (200 mL) and cooled to 5° C. A solution of pyridinium bromide perbromide (11.23 g, 0.035 mol) in THF (50 mL) was added dropwise and this mixture was stirred at 5° C. for 1 hr, at ambient temperature for 1 hr, and then evaporated to dryness. The residue was suspended in ethanol (150 mL) and cooled to 5° C. followed by the addition of sodium borohydride (3.59 g, 95 mmol). The reaction mixture was maintained at room temperature for 1 hr and then heated at reflux temperature for 1.5 hr. Water was carefully added and the ethanol evaporated. The aqueous mixture was neutralized and extracted with ethyl acetate (2×200 mL). The combined extracts were dried (MgSO4) and evaporated to a residue which was purified by column chromatography (silica, 15% ethyl acetate/hexane) to provide an amber syrup (8.2 g, 44%).

Step D: 2-[4-[2-(t-Butyldiphenylsiloxy)ethyl]phenyl]-3,4-dihydro-4-hydroxy-2H-thieno[3,2-e]-1,2-thiazine-6-sulfonamide 1,1-dioxide The product from Step C (8.2 g, 14 mmol) was dissolved in dry THF (50 mL) along with p-toluenesulfonic acid (0.5 g) and the solution cooled to 5° C. with an ice bath. Ethyl vinyl ether (2.62 mL, 27 mmol) was added and the reaction mixture was stirred for 0.5 hr. Saturated aqueous sodium bicarbonate (75 mL) was added to the reaction mixture followed extraction with ethyl acetate (2×50 mL). The combined extracts were dried (MgSO4) and evaporated to a residue which was purified by column chromatography (silica, 20% ethyl acetate/hexane) to provide an oil (7.62 g, 83%). This material was dissolved in dry THF (70 mL) under nitrogen and cooled to −65° C. n-BuLi (15 mL of a 1.76M solution, 26 mmol) was added dropwise, after 0.5 hr the reaction mixture was treated with sulfur dioxide until the dark solution turned yellow, stirring continued for 0.5 hr at room temperature. Evaporation of the solvent provided a residue which was suspended in water (50 mL) containing sodium acetate (7.7 g, 57 mmol) and hydroxylamine-0-sulfonic acid (3.88 g, 34 mmol ). This mixture was stirred at room temperature for 18 hr and then treated with 6N HCl (5 mL) for 3 hr followed by extraction with ethyl acetate (2×60 mL). The combined extracts were dried (MgSO4) and evaporated to a residue which was purified by column chromatography (silica, gradient: 4% to 5% ethanol/methylene chloride)

to give the desired product (1.78 g, 24%) as an amber syrup.

Step E:
4-Ethylamino-2-[4-[2-(t-butyldiphenylsiloxy)ethyl]-phenyl]-3,4-dihydro-2H-thieno-[3,2-e]-1,2-thiazine-6-sulfonamide 1,1-dioxide The product from Step D (1.77 g, 2.75 mmol) was dissolved in dry THF (15 mL) containing triethylamine (1.54 mL, 11 mmol) and cooled to 5° C. p-Toluenesulfonyl chloride (1.05 g, 5.5 mmol) was added and the mixture stirred at 5° C. for 4.5 hr. An excess of ethylamine was condensed into the reaction mixture which was stirred at ambient temperature for 18 hr and then evaporated to dryness. The residue was suspended in water and this mixture was extracted with ethyl acetate (2×50 mL). The combined extracts were dried (NaSO4) and purified by column chromatography (silica, 3.5% ethanol/methylene chloride) to provide 0.8 g (44%) of a solid: mp 66° C.

Step F:
4-Ethylamino-2-[4-(2-hydroxyethyl)phenyl]-3,4-dihydro-2H-thieno[3,2-e]-1,2-thiazine-6-sulfonamide 1,1-dioxide hydrochloride The product from Step E (0.7 g, 1.0 mmol) was dissolved in methanol (15 mL), tetra-n-butylammonium fluoride (12 mL of a 1.0M solution in THF, 12 mmol) was added, and the solution stirred at room temperature for 4 days. The reaction mixture was evaporated and the residue suspended in water; this mixture was basified with sodium bicarbonate and extracted with ethyl acetate 3×30 mL). The combined extracts were dried (molecular Sieves) and evaporated to a residue which was purified by column chromatography (silica, 8% ethanol/methylene chloride). The isolated material was treated with an excess of 1.5N ethanolic/hydrogen chloride. Evaporation provided a syrup which crystallized from isopropanol to give the desired product (0.22 g, 45%): mp 156°–159° C. Analysis: Calculated for $C_{16}H_{22}ClN_3O_5S_3$: C, 39.54; H, 4.98; N, 8.64. Found: C, 39.73; H, 5.08; N, 8.58.

By using modifications of the above procedure and using either aniline or 4-n-butylaniline in Step B and n-propylamine in Step E the following compounds were prepared.

1. 2-(4-n-Butyl phenyl)-3,4-dihydro-4-propylamino-2H-thieno[3,2-e]-1,2-thiazine-6-sulfonamide 1,1-dioxide hydrochloride, mp 148°–152° C.;
2. 3,4-Dihydro-2-phenyl-4-propylamino-2H-thieno[3,2-e]-1,2-thiazine-6-sulfonamide 1,1-dioxide tartrate, mp 123°–126° C.

By following the above general procedure but treating the product of Step D in a manner analogous to that described in Example 1, Steps H and I, the desired enantiomer (S configuration) of the product of Step D can be prepared. By treatment of this enantiomer as described in Steps E and F of the current Example the following compound can be prepared.

3. (R)-4-Ethylamino-2-[4-(2-hydroxyethyl)phenyl]-3,4-dihydro-2H-thieno[3,2-e]-1,2-thiazine-6-sulfonamide 1,1-dioxide hydrochloride By using modifications of the above procedure but replacing 4-(2-hydroxyethyl)-aniline with the appropriately substituted aniline in Step B, and using either ethylamine or n-propylamine in Step E, the following compounds can be prepared.

4. (R)-4-Ethylamino-2-(4-methoxy-phenyl)-3,4-dihydro-2H-thieno[3,2-e]-1,2-thiazine-6-sulfonamide 1,1-dioxide hydrochloride
5. (R)-4-Ethylamino-2-(4-hydroxy-phenyl)-3,4-dihydro-2H-thieno[3,2-e]-1,2-thiazine-6-sulfonamide 1,1-dioxide hydrochloride
6. (R)-3,4-Dihydro-2-(4-methoxy-phenyl)-4-propylamino-2H-thieno[3,2-e]-1,2-thiazine-6-sulfonamide 1,1-dioxide hydrochloride
7. (R)-3,4-Dihydro-2-(4-methoxy-phenyl)-4-propylamino-2H-thieno[3,2-e]-1,2-thiazine-6-sulfonamide 1,1-dioxide hydrochloride
8. (R)-4-Ethylamino-3,4-dihydro-2-(3-methyoxyphenyl)-2H-thieno[3,2-e]-1,2-thiazine-6-sulfonamide 1,1-dioxide hydrochloride
9. (R)-4-Ethylamino-3,4-dihydro-2-(3-methyoxyphenyl)-2H-thieno[3,2-e]-1,2-thiazine-6-sulfonamide 1,1-dioxide hydrochloride
10. (R)-3,4-Dihydro-2-(3-methoxy-phenyl)-4-propylamino-2H-thieno[3,2-e]-1,2-thiazine-6-sulfonamide 1,1-dioxide hydrochloride
11. (R)-3,4-Dihydro-2-(3-methoxy-phenyl)-4-propylamino-2H-thieno[3,2-e]-1,2-thiazine-6-sulfonamide 1,1-dioxide hydrochloride

EXAMPLE 5

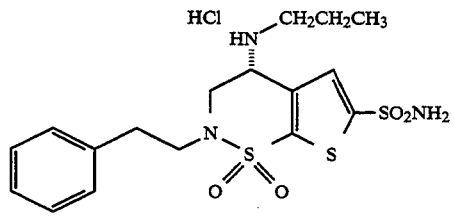

R-(+)-3,4-Dihydro-2-(2-phenylethyl)-4-propylamino-2H-thieno[3,2-e]-1,2-thiazine-6-sulfonamide 1,1-dioxide hydrochloride R—(+)-3,4-Dihydro-2-(2-phenylethyl)-4-propylamino-2H-thieno[3,2-e]-1,2-thiazine-6-sulfonamide 1,1-dioxide hydrochloride The following procedure is the invention of D. Dean et al. which is described and claimed in a concurrently filed, commonly assigned application.

Step A: 3-Acetyl-5-chloro-thiophene-2-sulfonamide

A 50-L, 5-necked flask equipped with a mechanical stirrer, a thermometer, and an 8 mm i.d. gas inlet tube was charged with the product from Example 4, Step A (1 kg, 3.54 mol) and ethyl acetate (20 L) and the pale yellow solution was cooled to 2° C. over 30 minutes using an ice-water bath. While the temperature was maintained below 7° C., chlorine gas was bubbled into the stirred solution, checking the reaction progress by TLC every 10 minutes. The reaction was complete after 30 minutes. Air was bubbled vigorously into the dark orange solution for 1 hour to purge excess chlorine, after which time the temperature was −2° C. While keeping the temperature below 10° C., ammonia was bubbled into the solution until TLC analysis indicated consumption of the intermediate sulfenyl chloride was complete. This required 1 hour and the addition of 120 grams of ammonia. The cold bath was removed and the mixture was again purged with air for 1 hour to remove excess ammonia. Water (5 L) and sodium tungstate dihydrate (583 g, 1.77 mol) were added to the orange suspension. 30% Hydrogen peroxide (7.2 L) was added from an additional funnel over 15 minutes, causing the temperature to rise to 15° C. The mixture was warmed to 20° C. over 30 minutes and then was stirred vigorously at ambient temperature for 15 hours without external temperature control. Water (5 L) was added, and the phases were split. The organic phase was washed sequentially with saturated aqueous sodium chloride (5 L), 10% aq. sodium bisulfite (5 L), saturated aqueous sodium chloride (5 L), 10% aq. sodium bicarbonate (10 L), and saturated aqueous sodium chloride (10 L). It was then dried over sodium sulfate (1 kg), filtered, and stripped of solvent by rotary evaporation. The residual solid was triturated with t-butyl methyl ether (3 L) and the mixture was chilled for 15 minutes. The solid was collected by filtration, washed with t-butyl methyl ether (1 L), and dried in air at ambient temperature to give the desired product (666 g, 79%): mp 178°–179° C.; Analysis. Calculated for $C_6H_6ClNO_3S_2$: C, 30.06; H, 2.52; N, 5.84; S, 26.75. Found: C, 30.19; H, 2.51; N, 5.80; S, 26.70.

Step B:
3-(2-Bromoacetyl)-5-chloro-thiophene-2-sulfonamide

A 50-L, 5-necked flask equipped with a mechanical stirrer, a thermometer, and a 1 L addition funnel was charged with the product from Step A (1.087 kg, 4.55 mol) and ethyl acetate (22 L). The pale yellow suspension was cooled to 1° C. over 45 minutes using an ice-water bath and 90% pyridinium bromide perbromide (1.305 kg, 3.67 mol) was added in one portion. Sulfuric acid (544 mL) was added via the addition funnel over 10 minutes causing the temperature to rise to 5° C. The reaction mixture was stirred and, after 1 hour, TLC analysis indicated complete reaction. Thirty minutes later, water (5 L) was added and the mixture was stirred for 5 minutes before the phases were split. The organic phase was washed with saturated aqueous sodium chloride until the pH of the wash was 3 (4×5 L), dried over sodium sulfate (1 kg), filtered, and stripped of solvent by rotary evaporation. The residue was triturated with methylene chloride (2 L) and chilled for 15 minutes before the solid was collected by filtration, washed with cold methylene chloride (2 L), and dried to give the desired product (1.041 kg, 72%): mp 147°–148° C. Analysis. Calculated for $C_6H_5BrClNO_3S_2$: C, 22.62; H, 1.58; N, 4.40; S, 20.13. Found: C, 22.66; H, 1.60; N, 4.35; S, 20.12.

Step C:
(S)-6-Chloro-3,4-dihydro-4-hydroxy-2H-thieno[3,2-e]-1,2-thiazine 1,1-dioxide A 50-L, 5-necked flask equipped with a mechanical stirrer and a thermometer was flushed with nitrogen overnight. Working under nitrogen, the flask was charged with the product from Step B (855 g, 2.68 mol) and t-butyl methyl ether (MTBE, 12.5 L). The stirred suspension was cooled to −40° C. using a dry-ice/2-propanol bath and (+)-β-chlorodiisopino-campheylborane (4.5 L of a 1.2M solution in MTBE, 5.4 mol) was added via a cannula over 30 minutes, causing the temperature to rise to −32° C. The reaction mixture was maintained between −25 to −20° C. for 3.5 hours. The mixture was warmed to 0° C. and 1M sodium hydroxide (11 L) was added from an addition funnel over 10 minutes, causing the temperature to rise to 22° C. The biphasic mixture was stirred vigorously at ambient temperature for 2 hours, after which TLC analysis indicated complete cyclization. The phases were split, and the dark aqueous layer was extracted with t-butyl methyl ether (3 L), acidified to pH 1 using concentrated hydrochloric acid, and extracted with ethyl acetate (2×4 L).

The combined ethyl acetate extracts were washed with saturated aqueous sodium chloride (3 L), dried over sodium sulfate (1 kg), filtered, and concentrated to a volume of about 1 liter by rotary evaporation, at which point toluene (2 L) was added. As the remainder of the ethyl acetate was removed, the product crystallized from toluene. It was collected by filtration, washed with toluene (2 L) and methylene chloride (2 L), and dried in air at ambient temperature (498 grams 77%): mp 126°–127° C.; $[\alpha]^{25}_D$ −5.9° (c=1, $CH_3OH$). Analysis. Calculated for $C_6H_6ClNO_3S_2$: C, 30.06; H, 2.52; N, 5.84. Found: C, 30.14; H, 2.56; N, 5.80.

Step D:
(S)-6-Chloro-3,4-dihydro-4-hydroxy-2-(2-phenylethyl)-2H-thieno[3,2-e]-1,2-thiazine 1,1-dioxide The product from Step C (1.5 g, 6.2 mmol) was added to a suspension of potassium carbonate (2.14 g, 15.5 mmol) in ethanol (25 mL) and phenethyl bromide (2.1 mL, 15.4 mmol) was added in three equal portions over a 24 hr period; stirring continued for 64 hr. The reaction mixture was evaporated and the residue suspended in water which was extracted with ethyl acetate (30 mL). The organic layer was dried ($MgSO_4$) and evaporated to a residue which was partially purified by column chromatography (silica, 3% ethanol/methylene chloride) to give 2.16 g of crude product (consisting of a 1:2 mixture of phenethyl bromide and the desired product) as a yellow oil; this material was used in the next step without further purification.

Step E:
(S)-3,4-Dihydro-4-hydroxy-2-(2-phenylethyl)-2H-thieno[3,2-e]-1,2thiazine-6-sulfonamide 1,1-dioxide The product from Step D (1.36 g, 3.96 mmol) was dissolved in dry THF (25 mL) along with p-toluenesulfonic acid (0.11 g, 0.6 mmol) and the solution cooled to 5° C. at which point ethyl vinyl ether (1.16 mL, 12.1 mmol) was added. After stirring this mixture for 40 min, saturated aqueous sodium bicarbonate (15 mL) was added followed by extraction with ethyl acetate (40 mL). The organic layer was dried ($Na_2SO_4$), evaporated, and the residue dissolved in THF (40 mL) under nitrogen. The solution was cooled to 60° C. and n-BuLi (4.1 mL of a 1.76M solution, 7.2 mmol) was added dropwise followed by stirring for 30 min and the introduction of sulfur dioxide until the green solution turned yellow. The cooling bath was removed and the reaction mixture stirred for 1 hr.

Evaporation of the solvent provided a residue which was suspended in water containing sodium acetate (4.89 g, 36 mmol) and hydroxylamine-O-sulfonic acid (2.73 g, 24 mmol); this mixture was stirred for 5 hr. The reaction mixture was acidified to pH 1 with 6N HCl and stirred at room temperature for 18 hr followed by extraction with ethyl acetate (2×50 mL). The combined extracts were dried ($MgSO_4$) and evaporated to a residue which was purified by column chromatography (silica, 5% ethanol/methylene chloride) to give the desired product as an oil which crystallized upon standing (1.14 g, 75%): mp 117°–119° C.

Step F:
R-(+)-3,4-Dihydro-2-(2-phenylethyl)-4-propylamino-2H-thieno[3,2-e]-1,2-thiazine-6-sulfonamide 1,1-dioxide hydrochloride The product from Step E (1.1 g, 2.80 mmol) was dissolved in THF (20 mL) containing triethylamine (1.58 mL, 11.3 mmol) and cooled to 5° C. p-Toluenesulfonyl chloride (1.07 g, 5.6 mmol) was added in small portions and the reaction mixture stirred for 4 hr at 5° C. The ice bath was removed and n-propylamine (30 mL) was added; this mixture was allowed to warm to room temperature and maintained at this temperature for 18 hr. The solvent was evaporated and the residue was extracted with ethyl acetate (4×25 mL). The combined extracts were washed with saturated aqueous sodium bicarbonate (3×25 mL), dried (Na$_2$SO$_4$), and evaporated to an oil which was purified by column chromatography (silica, 3% ethanol/methylene chloride) to give 0.62 g (52%) of the free base. This material was converted to the hydrochloride salt by treatment with ethanolic hydrogen chloride; recrystallization from ethanol/ether gave 0.55 g (42%) of the title compound as a white solid: mp 120° C.; [α]$_D$+13.6 (c=1.02, CH$_3$OH). Analysis: Calculated for C$_{17}$H$_{24}$ClN$_3$O$_4$S$_3$: C, 43.81; H, 5.19; N, 9.02. Found: C, 44.09; H, 5.31; N, 8.78.

By using modifications of the above procedure and replacing phenethyl bromide with the appropriately substituted benzyl halide in Step D, the following compounds can be prepared.
1. (R)-4-Ethylamino-3,4-dihydro-2-(4-methoxyphenylmethyl)-2H-thieno[3,2-e]-1,2-thiazine-6-sulfonamide 1,1-dioxide hydrochloride
2. (R)-4-Ethylamino-3,4-dihydro-2-(4-hydroxyphenylmethyl)-2H-thieno[3,2-e]-1,2-thiazine-6-sulfonamide 1,1-dioxide hydrochloride
3. (R)-4-Ethylamino-3,4-dihydro-2-(3-methoxyphenylmethyl)-2H-thieno[3,2-e]-1,2-thiazine-6-sulfonamide 1,1-dioxide hydrochloride
4. (R)-4-Ethylamino-3,4-dihydro-2-(4-hydroxyphenylmethyl)-2H-thieno[3,2-e]-1,2-thiazine-6-sulfonamide 1,1-dioxide hydrochloride

EXAMPLE 6

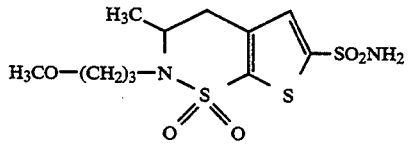

3,4-Dihydro-2-(3-methoxypropyl)-3-methyl-2H-thieno[3,2-e]-1,2-thiazine-6-sulfonamide 1,1-dioxide Step A: 3-(2-Hydroxypropyl)thiophene-2-sulfonamide To a solution of 3-(2-hydroxypropyl)thiophene (2.95 g, 20.77 mmol) in THF (25 mL) at −78° C. was added n-butyllithium (18.3 mL of a 2.5M solution, 45.69 mmol). This mixture was stirred at −78° C. for 1 hr and sulfur dioxide was added until the solution maintained a pH of 3. The reaction mixture was warmed to room temperature, stirred for 30 min, and evaporated to a residue which was dissolved in water (25 mL). Sodium acetate (5.1 g, 62.31 mmol) and hydroxylamine-O-sulfonic acid (7.0 g, 62.31 mmol) were added, the mixture stirred at room temperature for 18 hr, and the pH was adjusted to 8 with sodium bicarbonate. This solution was extracted with ethyl acetate (2×200 mL), the extracts were dried (MgSO$_4$) and evaporated to a residue which was purified by column chromatography (silica, 50% hexane/ethyl acetate) to give 1.9 g (42%) of the desired product.

Step B:
3,4-Dihydro-3-methyl-2H-thieno[3,2-e]-1,2-thiazine 1,1-dioxide

Triphenylphosphene (3.6 g, 13.76 mmol) and diethyl azodicarboxylate (2.2 mL, 13.76 mmol) were dissolved in THF (10 mL) and cooled to 0° C. To this was added a solution of the product from Step A (1.9 g, 8.6 mmol) in THF (10 mL) and the mixture was stirred at 0° C. for 3 hr. The solvent was evaporated and the residue dissolved in ethyl acetate (100 mL); this solution was washed with water (2×50 mL) and brine (2×50 mL), dried (MgSO$_4$), and evaporated to a syrup which was purified by column chromatography (silica, 1:2 hexane/ethyl acetate) to give the desired product (995 mg, 57%).

Step C:
3,4-Dihydro-2-(3-methoxypropyl)-3-methyl-2H-thieno[3,2-e]-1,2-thiazine 1,1-dioxide The product from Step B (800 mg, 3.94 mmol) was dissolved in DMF (10 mL) and the solution was cooled to −20° C. Sodium hydride (236 mg of an oil dispersion, 5.91 mmol) was added followed by 3-methoxypropyl bromide (1.8 mL, 11.82 mmol) and this mixture was warmed to 0° C. and stirred for 4 hr. The reaction mixture was poured into ice/water (50 mL) and extracted with ethyl acetate (2×100 mL). The combined extracts were washed with water (2×50 mL) and brine (2×50 mL), dried (MgSO$_4$) and evaporated to an oil which was purified by column chromatography (silica, 10% methanol/methylene chloride) to give the desired product (890 mg, 82%).

Step D:
3,4-Dihydro-2-(3-methoxypropyl)-3-methyl-2H-thieno[3,2-e]-1,2-thiazine-6-sulfonamide 1,1-dioxide To a solution of the product from Step C (890 mg, 3.23 mmol) in THF (8 mL) at −78° C. was added n-butyllithium (2.0 mL of a 2.5M solution, 4.85 mmol). This mixture was stirred at −78° C. for 40 min and sulfur dioxide was added until the solution maintained a pH of 3. The reaction mixture was warmed to room temperature, stirred for 30 min, and evaporated to a residue which was dissolved in water (20 mL). Sodium acetate (795 mg, 9.69 mmol) and hydroxylamine-O-sulfonic acid (1.0 g, 9.69 mmol) were added, the mixture stirred at room temperature for 18 hr, and the pH was adjusted to 8 with sodium bicarbonate. This solution was extracted with ethyl acetate (2×100 mL), the extracts were dried (MgSO$_4$) and evaporated to a residue which was purified by column chromatography (silica, 5:1 methanol/methylene chloride) to give the desired product. Recrystallization from methylene chloride gave a white solid (320 mg, 29%): mp 140° C. Analysis: Calculated for C$_{11}$H$_{18}$N$_2$O$_5$S$_3$: C, 37.27; H, 5.12; N,7.90. Found: C, 37.38; H, 5.18; N, 7.86.

By following the above general procedure but substituting the appropriate alkyl halide in Step C the following compounds were prepared:
1. 3,4-Dihydro-2,3-dimethyl-2H-thieno[3,2-e]-2-thiazine-6-sulfonamide 1,1-dioxide, mp 173°–175° C.;

2. 3,4-Dihydro-2-(2-methoxyethyl)-3-methyl-2H-thieno[3,2-e]-1,2-thiazine-6-sulfonamide 1,1-dioxide, mp 106°–108° C.

EXAMPLE 7

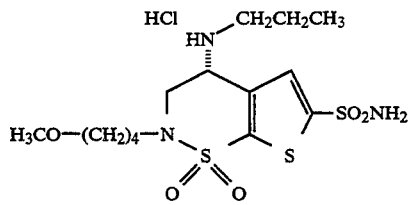

R-(+)-3,4-Dihydro-2-(4-methoxybutyl)-4-propylamino-2H-thieno[3,2-e]-1,2-thiazine-6-sulfonamide 1,1-dioxide hydrochloride

Step A: N-(1,1-Dimethylethyl)-3,4-dihydro-4-hydroxy-2-(4-methoxybutyl)-2H-thieno[3,2-e]-1,2-thiazine-6-sulfonamide 1,1-dioxide The product from Example 3, Step A (8.75 g, 0.26 mol) was dissolved in DMF (25 mL) and the solution was cooled to −0° C. Sodium hydride (1.56 g of an oil dispersion, 0.03 mol) was added, stirred for 30 min, and then 4-methoxybutyl bromide (8.6 g, 0.052 mol) in DMF (15 mL) was added; this mixture was warmed to room temperature and stirred for 15 hr. A saturated aqueous solution of ammonium chloride (20 mL) was added and the mixture was extracted with ethyl acetate (5×50 mL). The combined extracts were washed with brine (10 mL), dried (MgSO4) and evaporated to an oil which was purified by column chromatography (silica, gradient: 50% to 60% ethyl acetate/hexane) to give the desired product (9.5 g, 86%) as a yellow oil.

Step B: N-(1,1-Dimethylethyl)-3,4-dihydro-2-(4-methoxybutyl)-4-oxo-2H-thieno[3,2-e]-1,2-thiazine-6-sulfonamide 1,1-dioxide To a solution of the product from Step A (9.5 g, 0.022 mol) in acetone (20 mL) at −10° C. was added freshly prepared Jones reagent (10 mL) and the mixture was stirred at room temperature for 2 hr. The solvent was evaporated and saturated aqueous sodium bicarbonate was added until the pH of the solution was 6. The aqueous mixture was extracted with ethyl acetate (4×50 mL). The combined extracts were washed with brine (2×10 mL), dried (MgSO4) and evaporated to provide a yellow solid (7.5 g, 78%).

Step C: (S)-N-(1,1-Dimethylethyl)-3,4-dihydro-4-hydroxy-2-(4-methoxybutyl)-2H-thieno[3,2-e]-1,2-thiazine-6-sulfonamide 1,1-dioxide To a solution of (+)-β-chlorodiisopinocamphenylborane (28.01 g, 0.087 mol) in THF (60 mL) at −20° C. was added a solution of the product from Step B (7.4 g, 0.017 mol) in THF (90 mL); this mixture was stirred for 40 hr while maintaining this temperature. Diethanolamine (9.13 g, 0.087 mol) was added to the reaction mixture which was allowed to warm to room temperature and stirred at this temperature for 2 hr. Evaporation of the THF gave a residue which was dissolved in ethyl acetate (100 mL); this solution was washed with water (100 mL). The aqueous layer was separated and extracted with ethyl acetate (3×50 mL). The ethyl acetate extracts were combined, washed with brine (2×20 mL), dried (MgSO4), and evaporated to a residue which was purified by column chromatography (silica, 60% ethyl acetate/hexane) to give an oil (6.4 g, 86%).

Step D: R-(+)-3,4-Dihydro-2-(4-methoxybutyl)-4-propylamino-2H-thieno[3,2-e]-1,2-thiazine-6-sulfonamide 1,1-dioxide hydrochloride To a solution of the product from Step C (5.4 g, 0.013 mol) in THF (40 mL) at 0° C. was added triethylamine (5.38 g, 0.053 mol) followed by p-toluenesulfonyl chloride (5.07 g, 0.027 mol) and the mixture was stirred for 2 hr. The reaction mixture was divided into two equal volumes, one of which was treated with propylamine (15 mL) at 0° C. for 15 hr. The excess propylamine was evaporated and the solution diluted with water (50 mL). The organic layer was separated and the aqueous layer was extracted with ethyl acetate (3×50 mL). The combined extracts were washed with brine (20 mL), dried (MgSO4), and evaporated to a crude product which was purified by column chromatography (silica, gradient: 50% to 70% ethyl acetate/hexane). The free base was dissolved in ethanol (10 mL) and treated with ethanolic hydrogen chloride. Evaporation gave a solid which was recrystallized from isopropanol to give the desired product as a white solid (1.4 g, 26%): mp 183°–185° C.; $[\alpha]_D +27.2°$ (c=0.43, CH3OH). Analysis: Calculated for $C_{14}H_{26}ClN_3O_5S_3 \cdot 0.5\ H_2O$: C, 36.79; H, 5.95; N, 9.19. Found: C, 37.08; H, 6.34; N, 8.82.

EXAMPLE 8

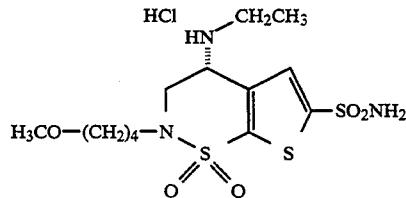

R-(+)-4-Ethylamino-3,4-dihydro-2-(4-methoxybutyl)-2H-thieno[3,2-e]-1,2-thiazine-6-sulfonamide 1,1-dioxide hydrochloride The second portion of the intermediate tosylate prepared in Example 7, Step D was treated with ethylamine (18 mL) at 0° C. for 15 hr. By proceeding in a manner analogous to that already described in Example 7, Step D the title compound was obtained (2.4 g, 46%): mp 129°–130° C.; $[\alpha]_D +23.6°$ (c=0.49, CH3OH). Analysis. Calculated for $C_{13}H_{24}ClN_3O_5S_3$: C, 35.97; H, 5.57; N, 9.68. Found: C, 35.80; H, 5.84; N, 9.41.

Using modifications of the procedures described above and in Examples 7 but substituting the appropriate alkyl halide in Step A and the desired alkylamine in Step D the following compounds were prepared:

1. R-(+)-4-Ethylamino-3,4-dihydro-2-(6-hydroxyhexyl)-2H-thieno[3,2-e]-1,2-thiazine-6-sulfonamide 1,1-dioxide hydrochloride, mp 200°–201° C;
2. R-(+)-4-Allylamino-3,4-dihydro-2-(2-methylpropyl)-2H-thieno[3,2-e]-1,2-thiazine-6-sulfonamide 1,1-dioxide hydrochloride, 202°–205° C.;
3. R-(+)-3,4-Dihydro-2-(4-hydroxybutyl)-4-propylamino-2H-thieno[3,2-e]-1,2-thiazine-6-sulfonamide 1,1-dioxide hydrochloride, mp 197°–198° C.;

4. R-(+)-3,4-Dihydro-2-(2-methylpropyl)-4-propylamino-2H-thieno[3,2-e]-1,2-thiazine-6-sulfonamide 1,1-dioxide hydrochloride, mp 163°–165° C.;

5. R-(+)-4-Ethylamino-3,4-dihydro-2-(2-methylpropyl)-2H-thieno[3,2-e]-1,2-thiazine-6-sulfonamide 1,1-dioxide hydrochloride, mp 170° C.;

6. R-(+)-4-Cyclopropylmethylamino-3,4-dihydro-2-(2-methylpropyl)-2H-thieno[3,2-e]-1,2-thiazine-6-sulfonamide 1,1-dioxide hydrochloride, mp 162°–164° C.

7. R-(+)-4-Ethylamino-3,4-dihydro-2-(3-methoxybutyl)-2H-thieno[3,2-e]-1,2-thiazine-6-sulfonamide 1,1-dioxide hydrochloride, mp 207°–209° C.;

8. R-(+)-3,4-Dihydro-2-(3-methoxypropyl)-4-(2-methoxyethyl)amino-2H-thieno[3,2-e]-1,2-thiazine-6-sulfonamide 1,1-dioxide hydrochloride, mp 185°–187° C.;

9. R-(+)-3,4-Dihydro-2-(3-methoxybutyl)-4-n-propylamino-2H-thieno[3,2-e]-1,2-thiazine-6-sulfonamide 1,1-dioxide hydrochloride, mp 156°–158° C.;

10. R-(+)-4-Ethylamino-3,4-dihydro-2-(4-hydroxybutyl)-2H-thieno[3,2-e]-1,2-thiazine-6-sulfonamide 1,1-dioxide hydrochloride, mp 130° C.

Using modifications of the procedures described above and in Examples 7 but substituting the appropriate alkyl halide in Step A and the desired alkylamine in Step D the following compound can be prepared:

11. (R)-3,4-Dihydro-2-(3-hydroxypropyl)-4-(2-methylpropyl)amino-2-H-thieno[3,2-e]-1,2-thiazine-6-sulfonamide 1,1-dioxide hydrochloride.

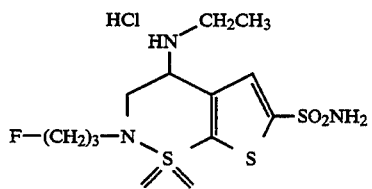

4-Ethylamino-2-(3-fluoropropyl)3,4-dihydro-2H-thieno[3,2-e]-1,2-thiazine-6-sulfonamide 1,1-dioxide hydrochloride Step A:
2-(3-Fluoropropyl)-3,4-dihydro-4-hydroxy-N-(1,1-dimethylethyl)-2H-thieno[3,2-e]-1,2-thiazine-6-sulfonamide 1,1-dioxide The product from Example 3, Step A (1.52 g, 4.47 mmol) was dissolved in DMF (10 mL) and the solution was cooled to 0° C. Sodium hydride (0.32 g of an oil dispersion, 8.04 mmol) was added, stirred for 30 min, and then 3-fluoropropyl bromide (1.13 g, 8.04 mmol) was added; this mixture was warmed to room temperature and stirred for 4 hr. A saturated aqueous solution of ammonium chloride (20 mL) was added and the mixture was extracted with ethyl acetate (4×50 mL). The combined extracts were washed with brine (10 mL), dried (MgSO4) and evaporated to an oil which was dissolved in trifluoroacetic acid (20 mL) and stirred at room temperature for 18 hr. The mixture was evaporated to a residue which was purified by column chromatography (silica, gradient: 30% to 60% ethyl acetate/hexane) to give the desired product (1.0 g, 65%) as an oil.

Step B:
4-Ethylamino-3,4-dihydro-2-(3-fluoropropyl)-2H-thieno[3,2-e]-1,2-thiazine-6-sulfonamide 1,1 -dioxide hydrochloride A solution of the product from Step A (0.99 g, 2.87 mmol) in THF (6.0 mL) at 0° C. was treated with p-toluenesulfonyl chloride (1.09 g, 5.75 mmol) and subsequently ethylamine (5 mL) in a manner identical to that described in Example 7, Step D to give the desired compound (700 mg, recrystallized from ethyl acetate/methylene chloride): mp 238°–239° C. Analysis. Calculated for C11H19ClFN3O4S3: C, 32.38; H, 4.69; N, 10.30. Found: C, 32.52; H, 4.90; N, 0.29.

Using modifications of the above procedure but substituting the appropriate alkyl halide in Step A and using either ethylamine or n-propylamine in Step B the following compounds were prepared:

1. 3,4-Dihydro-2-propyl-4-propylamino-2H-thieno[3,2-e]-1,2-thiazine-6-sulfonamide 1,1-dioxide hydrochloride, mp 130°–133° C.;

2. 3,4-Dihydro-4-(2 -methylpropyl)amino-2-propyl-2H-thieno[3,2-e]-1,2-thiazine-6-sulfonamide 1,1-dioxide hydrochloride hemihydrate, mp 145°–147° C.;

3. 3,4-Dihydro-2-(3-hydroxypropyl)-4-n-propylamino-2H-thieno[3,2-e]-1,2-thiazine-6-sulfonamide 1,1-dioxide hydrochloride, mp 98°–100° C.;

4. 3,4-Dihydro-2-(3-hydroxypropyl)-4-(2-methylpropyl)amino-2H-thieno[3,2-e]-1,2-thiazine-6-sulfonamide 1,1-dioxide hydrochloride hemihydrate, mp 110°–112° C.;

5. 3,4-Dihydro-2-(2-hydroxypropyl)-4-propylamino-2H-thieno[3,2-e]-1,2-thiazine-6-sulfonamide 1,1-dioxide hydrochloride, mp 194°–200° C.;

6. 3,4-Dihydro-2-(2-hydroxypropyl)-4-(2-methylpropyl)amino-2H-thieno[3.2-e]-1,2-thiazine-6-sulfonamide 1,1-dioxide hydrochloride, mp 181°–183° C.;

7. 3,4-Dihydro-2-(4-hydroxybutyl)-4-(2-methylpropyl)amino-2H-thieno[3,2-e]-1,2-thiazine-6-sulfonamide 1,1-dioxide hydrochloride, mp 202° C.;

8. 4-Ethylamino-3,4-dihydro-2-(3-hydroxybutyl)-2H-thieno[3,2-e]-1,2-thiazine-6-sulfonamide 1,1-dioxide hydrochloride, mp 73°–75° C.;

9. 4-Ethylamino-3,4-dihydro-2-(4-hydroxypentyl)-4-n-propylamino-2H -thieno[3,2-e]-1,2-thiazine-6-sulfonamide 1,1-dioxide hydrochloride, mp 187°–188° C.;

10. 3,4-Dihydro-2-(5-hydroxyhexyl)-4-(2-methylpropyl)amino-2H-thieno[3,2-thiazine-6-sulfonamide 1,1-dioxide hydrochloride, mp 187°–188° C.;

11. 4-Ethylamino-3,4-dihydro-2-(2,3,4,5-tetrahydrofuran-2-yl)methyl-4-2H-thieno[3,2-e]-1,2-thiazine-6-sulfonamide 1,1-dioxide hydrochloride, mp 142°–144° C.

EXAMPLE 10

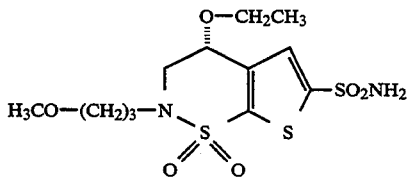

-continued

R-(−)-4-Ethoxy-3,4-dihydro-2-(3-methoxypropyl)-2H-thieno[3,2-e]-1,2-thiazine-6-sulfonamide 1,1-dioxide hydrochloride Step A:
(R)-3,4-Dihydro-4-hydroxy-2-(3-methoxypropyl)-2H-thieno[3,2-e]-1,2-thiazine-6-sulfonamide 1,1-dioxide To a solution of (−)-β-chlorodiisopinocampheylborane (20.4 g, 63.5 mmol) in THF (20 mL) at −20° C. was added a solution of the product from Example 1, Step H (4.5 g, 12.7 mmol) in THF (60 mL) at −20° C.; this mixture was stirred for 48 hr maintaining this temperature. Diethanolamine (6,6 g, 63.5 mmol) was added and the solution allowed to warm to room temperature. The solvent was evaporated and the residue suspended in water (50 mL). This mixture was extracted with ethyl acetate (5×50 mL), and the combined extracts were washed with brine (15 mL), dried (MgSO4), and evaporated to a syrup which was purified by column chromatography (silica, gradient: 50% to 60% ethyl acetate/-hexane) to give a white solid (3.9 g, 85%); mp 109°–111° C. Analysis: Calculated for $C_{10}H_{16}N_2O_6S_3$: C, 33.69; H, 4.53; N, 7.86. Found: C, 33.74; H, 4.48; N, 7.85.

Step B:
R-(−)-4-Ethoxy-3,4-dihydro-2-(3-methoxypropyl)-2H-thieno[3,2-e]-1,2-thiazine-6-sulfonamide 1,1-dioxide hydrochloride To a solution of the product from Part A (2.81 g, 7.9 mmol) in acetonitrile (10 mL) at room temperature was added dimethylformamide dimethyl acetal (1.16 mL, 8.6 mmol); this solution was stirred for 2 hr and evaporated to dryness. The crude product was purified by chromatography (silica, 50% ethyl acetate/hexane) to give the desired protected sulfonamide derivative. This compound (2.54 g, 5.6 mmol) was dissolved in DMF (15 mL), cooled to 0° C., and sodium hydride (0.33 9 of a 60% oil dispersion, 8.33 mmol) was added. After stirring for 30 min, ethyl iodide (1.3 g, 8.3 mmol) was added and stirring continued, but at room temperature, for 2 hr. A saturated aqueous solution of ammonium chloride (50 mL) was added and the mixture extracted with ethyl acetate (3×50 mL). The combined extracts were washed with brine (20 mL), dried (MgSO4), and evaporated to a residue which was dissolved in ethanol (3 mL), acetic acid (6 mL) and hydrazine (1.4 mL) were added and the mixture was heated at 55° C. for 24 hr. After cooling to room temperature, saturated aqueous sodium bicarbonate (30 mL) was added and the mixture was extracted with ethyl acetate (4×50 mL) The combined extracts were washed with brine (10 mL), dried (MgSO4), and evaporated to a residue which was purified by column chromatography (silica, gradient: 30% to 50% ethyl acetate/hexane) to give a syrup (500 mg). $[\alpha]_D$ −3.91° (c=0.67, CH3OH). Analysis. Calculated for $C_{12}H_{20}N_2O_6S_3$: C, 37.48; H, 5.24; N, 7.29. Found: C, 37.61; H, 5.25; N, 7.18.

EXAMPLE 11

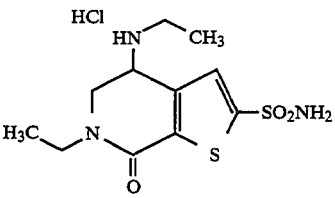

6-Ethyl-4-ethylamino-4,5,6,7-tetrahydro-7-oxo-thieno[2,3-b]pyridine-2-sulfonamide hydrochloride Step A: 6-Ethyl-4,5,6,7-tetrahydro-4-(trifluoroacetamino)-7-oxo-thieno[2,3-b]pyridine After cooling a solution of 4,5,6,7-tetrahydro-4-(trifluoroacetamino)-7-oxo-thieno[2,3-b]pyridine (1.0 g, 3.8 mmol) in DMF (10 mL) to −20° C., sodium hydride (273 mg, 11.4 mmol of a 60% oil dispersion) was added followed by ethyl bromide (1.7 mL, 22.7 mmol). This mixture was allowed to warm to room temperature. Stirring continued at this temperature for an additional hour and then the mixture was poured into ice water (100 mL). This aqueous mixture was extracted with ethyl acetate (4×100 mL) and the combined extracts were washed with brine (2×50 mL), dried (MgSO4), and concentrated to a crude oil which was purified by column chromatography (silica, 5% methanol/methylene chloride) to give a yellow solid (0.85 g, 77%): mp 136°–138° C.

Step B:
6-Ethyl-4-amino-4,5,6,7-tetrahydro-7-oxo-thieno[2,3-b]pyridine

To a solution of the product from Step A (4.5 g, 15.4 mmol) in 50% aqueous methanol (80 mL) was added potassium carbonate (3.2 g, 23 mmol) and the mixture stirred at room temperature for 5 hr. The methanol was evaporated and the remaining aqueous mixture was acidified (pH 3), extracted with ethyl acetate (100 mL), the pH was adjusted to 9 and again extracted with ethyl acetate (3×200 mL). The combined extracts were evaporated to an oil which was purified by column chromatography (silica, 5% methanol/methylene chloride) to give the desired product as a yellow oil (2.7 g, 70%).

Step C:
6-Ethyl-4-ethylamino-4,5,6,7-tetrahydro-7-oxo-thieno[2,3-b]pyridine

To a solution of the product from Step B (2.7 g, 13.8 mmol) in methanol (20 mL) at room temperature was added acetic acid (790 mL, 13.8 mmol) and sodium cyanoborohydride (867 mg, 13.8 mmol). After stirring this mixture for 18 hr concentrated HCl (1 mL) was added; when the evolution of gas ceased, the pH of the mixture was adjusted to 9 with 50% NaOH. The solvent was evaporated and the residue dissolved in ethyl acetate (200 mL); this solution was washed with brine (2×50 mL), dried (MgSO4), and evaporated to an oil which was purified by column chromatography (silica, 5% methanol/methylene chloride) to give the desired product (1.85 g, 62%).

Step D:
6-Ethyl-4-ethylamino-4,5,6,7-tetrahydro-7-oxo-thieno[2,3-b]pyridine-2-sulfonamide hydrochloride After cooling a solution of the product from Step C (1.7 g, 7.6 mmol) in THF (10 mL) to −78° C., a 1.7M solution of t-butyllithium in pentane (13.4 mL, 22.8 mmol) was added and the reaction mixture stirred at −78° C. for 1 hr. Sulfur dioxide gas was passed through the reaction mixture until a pH of 3 was maintained. The mixture was allowed to warm to room temperature, and after stirring for 30 min was evaporated to a residue which was dissolved in water (100 mL). Sodium acetate (1.87 g, 22.8 mmol) and hydroxylamine-O-sulfonic acid (2.6 g, 22.8mmol) were added and the mixture stirred at room temperature for 18 hr and basified to pH 8. This aqueous mixture was extracted with ethyl acetate (3×200 mL) and the combined extracts were washed with saturated aqueous sodium bicarbonate (2×50 mL), dried (MgSO4), and evaporated to an oil which was purified by column chromatography (silica, 5% methanol/methylene chloride) to give the free base as a foam (700 mg, 37%). This material was converted to the hydrochloride salt by treatment with ethanolic/hydrogen chloride followed by recrystallization from methanol/methylene chloride (1:40) to give 600 mg of the desired product: mp 235° C. Analysis: Calculated for $C_{11}H_{18}ClN_3OS_2$: C, 38.88; H, 5.34; N, 12.30. Found: C, 38.98; H, 5.35; N, 12.26.

EXAMPLE 12

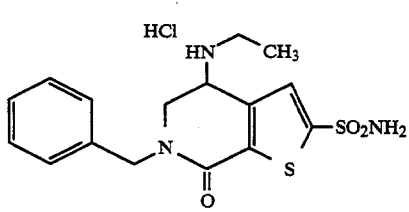

4-Ethylamino-4,5,6,7-tetrahydro-7-oxo-6-(phenylmethyl)-thieno[2,3-b]pyridine-2-sulfonamide hydrochloride By following the same procedure as that described in Example 11, but substituting benzylchloride for ethyl bromide in Step A, the desired compound was obtained as a crystalline solid: mp 269–270C. Analysis: Calculated for $C_{16}H_{20}ClN_3O_3S_2 \cdot H_2C$, 45.67; H, 5.28; N, 10.00. Found: C, 45.65; H, 5.25; N, 10.11.

EXAMPLE 13

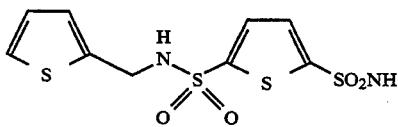

N-(2-Thienyl)methyl-2,5-thiophenedisulfonamide

To a solution of 5-sulfamoyl-thiophene-2-sulfonyl chloride (0.80 g, 3.1 mmol) in ethanol (10 mL) at 0° C. was added 2-thiophenemethylamine (0.67 mL, 6.51 mmol) and this mixture stirred at room temperature for 18 hr. After evaporation of solvent the residue was dissolved in ethyl acetate (200 mL) and this solution was washed with saturated aqueous sodium bicarbonate (2×50 mL), dried (MgSO4), and evaporated to a crude material which was purified by column chromatography (silica, 5% methanol/methylene chloride) and recrystallization [methanol/methylene chloride (1:50)] to give the desired product (450 mg, 45%): mp 146°–148° C. Analysis: Calculated for $C_9H_{10}N_2O_4S_4$: C, 31.94; H, 2.98; N, 8.28. Found: C, 32.00; H, 2.96; N, 8.29.

By following the above procedure but using instead the appropriate arylalkylamine the following compounds were prepared:
1. N-(4-Trifluoromethylphenyl)methyl-2,5-thiophenedisulfonamide, mp 163°–164° C.;
2. N-(3,5-Dichlorophenyl)methyl-2,5-thiophenedisulfonamide, mp 141°–142° C.;
3. N-(3,4-Dichlorophenyl)methyl-2,5-thiophenedisulfonamide, mp 178°–179° C.;
4. N-(4-Methoxyphenyl)methyl-2,5-thiophenedisulfonamide, mp 149°–150° C.;
5. N-(4-Fluorophenyl)methyl-2,5-thiophenedisulfonamide, mp 166°–167° C.
6. N-[[4-(4-Morpholinyl methyl) phenyl]methyl]-2,5-thiophene disulfonamide, mp 161°–162° C.
7. N-[[3-(4-Morpholinylmethyl)phenyl]methyl]-2,5-thiophenedisulfonamide hydrochloride, mp 166°–168° C.

EXAMPLE 14

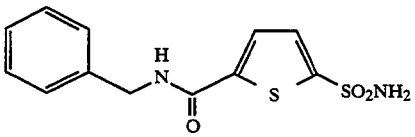

N-(Phenylmethyl)-5-(aminosulfonyl)-thiophene-2-carboxamide

To a mixture of benzylamine (0.91 mL, 8.5 mmol) and triethylamine (0.33 mL, 2.41 mmol) was added bis(triphenylphosphine)palladium(II) bromide (0.066 g, 0.08 mmol) and this mixture was stirred at 100° C. under an atmosphere of carbon monoxide for 19 hr. The reaction mixture was diluted with ethyl acetate (50 mL) and washed with water (50 mL). The aqueous phase was washed with ethyl acetate (2×50 mL) and the combined organic phase was dried (MgSO4) and concentrated. The solid was collected and washed with 50% ethyl acetate/hexane (40 mL) and hexane (30 mL). Concentration of the filtrate provided additional solid to give a total of 0.56 g (23 %) of crude product. Recrystallization from ethyl acetate/ethanol/hexane (1:1.5:1) gave the desired product: mp 203° C. Analysis: Calculated for $C_{12}H_{12}N_2O_3S_2$: C, 48:65; H, 4.05; N, 9.46. Found: C, 48.50; H, 4.11; N, 9.37.

By following the above general procedure, the following compounds were prepared:
1. N-[(2-Thienyl)methyl)]-5-(amino-sulfonyl)-thiophene-2-carboxamide, mp 146°–148° C.
2. N-(methyl )-N-(phenylmethyl )-5-(amino-sulfonyl)-thiophene-2-carboxamide mp 173°–173.5° C.

Using the procedures described in equations 1 to 13, the Examples 1 to 14 and well known procedures, one skilled in the art can prepare the compounds disclosed herein and those listed in Tables 1 to 3.

In the Tables the following symbols correspond to the chemical structures: Me is $CH_3$; Et is $CH_2CH_3$; n-Pr is $CH_2CH_2CH_3$; i-Pr is $CH(CH_3)_2$; i-Bu is $CH_2CH(CH_3)_2$; t-Bu is $C(CH_3)_3$ and Ph is $C_6H_5$.

TABLE 1

Structure: R₁R₂N-CH₂-C(R₂)-[thiophene fused ring with G]-SO₂NH₂

| G | R₁ | R₂ |
|---|---|---|
| SO₂ | CH₂CO₂-i-Pr | NH-n-Pr |
| SO₂ | CH₂CO₂-i-Pr | NHEt |
| SO₂ | (CH₂)₃CO₂-i-Pr | NHEt |
| SO₂ | (CH₂)₂N(CH₂CH₂)₂O | H |
| SO₂ | (CH₂)₂N(CH₂CH₂)₂O | OCH₂CH₂OH |
| SO₂ | (CH₂)₂N(CH₂CH₂)₂O | OCH₂CH₂OMe |
| SO₂ | (CH₂)₂N(CH₂CH₂)₂O | CH₂CH₃ |
| SO₂ | (CH₂)₂N(CH₂CH₂)₂O | CH₂OMe |
| SO₂ | (CH₂)₂N(CH₂CH₂)₂S | NHEt |
| SO₂ | (CH₂)₂N(CH₂CH₂)₂SO₂ | OH |
| SO₂ | CH₂CCH | NHEt |
| SO₂ | CH₂CCCH₂OCH₃ | NHEt |
| SO₂ | CH₂CONHMe | NHEt |
| SO₂ | (CH₂)₂CONH(CH₂)₂OH | NHEt |
| SO₂ | C₆H₄—(3-OEt) | NHEt |
| SO₂ | C₆H₄—(3-OH) | NHEt |
| SO₂ | C₆H₄—(3-OH) | NH-n-Pr |
| SO₂ | C₆H₄—(3-OMe) | NHEt |
| SO₂ | C₆H₄—(4-OH) | NHEt |
| SO₂ | C₆H₄—(4-OMe) | NHEt |
| SO₂ | C₆H₄—(3-OCHF₂) | NHEt |
| SO₂ | C₆H₄—(4-SO₂Me) | NHEt |
| SO₂ | C₆H₄—(4-NHCOMe) | NHEt |
| SO₂ | C₆H₄—(4-CONMe₂) | NHEt |
| SO₂ | C₆H₃—(4-OH)—(3-CH₂NMe₂) | OEt |
| SO₂ | C₆H₃—(4-OH)—(3-CH₂NMe₂) | H |
| SO₂ | C₆H₃—(3,4-OH) | NHEt |
| SO₂ | C₆H₃—(3,4-OMe) | NHEt |
| SO₂ | C₆H₄—(4-COCH₃) | NHEt |
| SO₂ | CH₂C₆H₄—(3,4-OMe) | NHEt |
| SO₂ | CH₂C₆H₃—(4-OH)—(3-CH₂NMe₂) | OEt |
| SO₂ | CH₂C₆H₄—(4-OMe) | NHEt |
| SO₂ | CH₂C₆H₄—(3-OH) | NHEt |
| SO₂ | CH₂[(2-CO₂Et)-pyridin-4-yl] | NHEt |
| SO₂ | CH₂[(5-CO₂iPr)-thieno-2-yl] | NHEt |
| SO₂ | (CH₂)₃OH | OH |
| SO₂ | (CH₂)₄OH | OH |
| SO₂ | (CH₂)₅OH | OH |
| SO₂ | (CH₂)₆OH | OH |
| SO₂ | (CH₂)₄OH | OEt |
| SO₂ | (CH₂)₄OH | NH-n-Pr |
| SO₂ | (CH₂)₄OH | NH-i-Bu |
| SO₂ | (CH₂)₃OCH₃ | OEt |
| SO₂ | (CH₂)₂OCH₃ | OEt |
| SO₂ | CH₂-2-thienyl | OH |
| SO₂ | CH₂—C₆H₅ | OH |
| SO₂ | (CH₂)₂CH(OH)CH₃ | NHEt |
| SO₂ | (CH₂)₃CH(OH)CH₃ | NHEt |
| SO₂ | (CH₂)₂CH(OCH₃)CH₃ | NHEt |
| SO₂ | (CH₂)₃OH | H |
| SO₂ | (CH₂)₃OCH₃ | H |
| SO₂ | (CH₂)₃OCOCH₃ | NHEt |
| SO₂ | (CH₂)₄OCOCH₃ | NHEt |
| SO₂ | (CH₂)₂CO₂Et | NHEt |
| SO₂ | (CH₂)₃CO₂Et | NHEt |
| SO₂ | (CH₂)₅CO₂Et | NHEt |
| SO₂ | (CH₂)₄CO₂-i-Pr | NHEt |
| SO₂ | (CH₂)₅CH₃ | NHEt |
| SO₂ | (CH₂)₄CH₃ | NHEt |
| SO₂ | (CH₂)₃CH(CH₃)₂ | NHEt |
| SO₂ | CH₂-2-thiazole | OH |
| SO₂ | CH₂-2-oxazole | OH |
| SO₂ | CH₂-2-pyrimidine | OH |
| SO₂ | CH₂-3-pyridazine | OH |
| SO₂ | CH₂-2-pyrazine | OH |
| SO₂ | CH₂-3-isothiazole | OH |
| SO₂ | CH₂-3-isoxazole | OH |
| CO | (CH₂)₃CO₂-i-Pr | NHEt |
| CO | C₆H₄—(3-OH) | NHEt |
| CO | C₆H₄—(3-OH) | NH-n-Pr |
| CO | C₆H₄—(3-OMe) | NHEt |
| CO | C₆H₄—(4-OH) | NHEt |
| CO | C₆H₄—(4-OMe) | NHEt |
| CO | C₆H₄—(3-OCHF₂) | NHEt |

TABLE 1-continued

| G | R₁ | R₂ |
|---|---|---|
| CO | C₆H₄—(4-SO₂Me) | NHEt |
| CO | C₆H₃—(4-OH)—(3-CH₂NMe₂) | OEt |
| CO | C₆H₃—(4-OH)—(3-CH₂NMe₂) | H |
| CO | C₆H₃—(3,4-OH) | NHEt |
| CO | C₆H₃—(3,4-OMe) | NHEt |
| CO | C₆H₄—(4-COCH₃) | NHEt |
| CO | CH₂C₆H₄—(3,4-OMe) | NHEt |
| CO | CH₂C₆H₃—(4-OH)—(3-CH₂NMe₂) | OEt |
| CO | CH₂C₆H₄—(4-OMe) | NHEt |
| CO | CH₂C₆H₄—(3-OH) | NHEt |
| CO | CH₂[(2-CO₂Et)-pyridin-4-yl] | NHEt |
| CO | CH₂[(5-CO₂iPr)-thieno-2-yl] | NHEt |

TABLE 2

| G | R₁ | R₂ | R₃ |
|---|---|---|---|
| SO₂ | (CH₂)₂N(CH₂CH₂)₂O | H | COCH₃ |
| SO₂ | CH₂C₆H₄—(3-OH) | CH₃ | H |
| SO₂ | CH₂C₆H₄—(3-OMe) | H | H |
| SO₂ | CH₂C₆H₄—(4-OH) | H | CH₃ |
| SO₂ | CH₂C₆H₄—(4-OMe) | H | H |
| SO₂ | CH₂C₆H₄—(4-OH) | H | CH₂OEt |
| SO₂ | CH₂C₆H₄—(4-CONHMe) | H | CH₃ |
| SO₂ | CH₂C₆H₄—(4-SO₂NMe₂) | H | H |
| SO₂ | CH₂C₆H₄—(3-SO₂Me) | H | CH₃ |
| SO₂ | CH₂C₆H₄—(4-OCHF₂) | CH₃ | H |
| SO₂ | CH₂C₆H₃—(4-OH)-3-(CH₂NMe₂) | CH₃ | CH₃ |
| SO₂ | CH₂C₆H₄—(3-NHCOMe) | H | CH₃ |
| SO₂ | CH₂-4-pyridinyl | H | CH₃ |
| SO₂ | CH₂-2-pyridinyl | H | CH₃ |
| SO₂ | CH₂-2-thienyl | H | CH₃ |
| SO₂ | CH₂—(5-Me-2-thienyl) | H | H |
| CO | (CH₂)₂N(CH₂CH₂)₂O | H | COCH₃ |
| CO | CH₂C₆H₄—(3-OH) | CH₃ | H |
| CO | CH₂C₆H₄—(3-OMe) | H | H |
| CO | CH₂C₆H₄—(4-OH) | H | CH₃ |
| CO | CH₂C₆H₄—(4-OMe) | H | H |
| CO | CH₂C₆H₄—(4-OH) | H | CH₃ |
| CO | CH₂C₆H₄—(4-CONHMe) | H | CH₃ |
| CO | CH₂C₆H₄—(4-SO₂NMe₂) | H | H |
| CO | CH₂C₆H₄—(3-SO₂Me) | H | CH₃ |
| CO | CH₂C₆H₄—(4-OCHF₂) | CH₃ | H |
| CO | CH₂C₆H₃—(4-OH)-3-(CH₂NMe₂) | CH₃ | CH₃ |
| CO | CH₂C₆H₄—(3-NHCOMe) | H | CH₃ |
| CO | CH₂-4-pyridinyl | H | CH₃ |
| CO | CH₂-2-pyridinyl | H | CH₃ |
| CO | CH₂-2-thienyl | H | CH₃ |
| CO | CH₂—(5-Me-2-thienyl) | H | H |

TABLE 3

| R₁ | R₂ | R₃ |
|---|---|---|
| CH₃ | H | CH₂N(CH₂CH₂)₂O |
| (CH₂)₃OMe | H | CH₂N(CH₂CH₂)₂O |
| CH₂N(CH₂CH₂)₂O | H | CH₂OH |
| CH₂N(CH₂CH₂)₂O | H | CH₂OMe |
| CH₂N(CH₂CH₂)₂O | H | CH₃ |

TABLE 3-continued

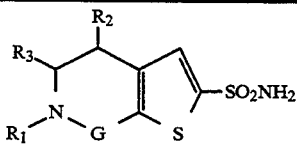

| R₁ | R₂ | R₃ |
|---|---|---|
| (CH₂)₃OMe | H | CH₂NHCH₃ |
| (CH₂)₃OMe | H | CH₂NH(CH₂)₂OMe |
| (CH₂)₄OMe | NHEt | CH₃ |
| C₆H₄—(4-OH) | NHEt | CH₃ |
| C₆H₄—(3-OMe) | NHEt | CH₃ |
| CH₂C₆H₄—(4-OH) | NHEt | CH₃ |

EXAMPLE 15

Ophthalmic Suspension

| Ingredient | Concentration (wt %) |
|---|---|
| 3,4-Dihydro-4-methoxy-2-methyl-2H-thieno[3,2-e]-1,2-thiazine-6-sulfonamide-1,1-dioxide (Compound) | 3.0% |
| Hydroxypropylmethylcellulose | 0.5% |
| Dibasic Sodium Phosphate | 0.2% |
| Disodium Edetate | 0.01% |
| Sodium Chloride | 0.8% |
| Purified Water | q.s |
| Benzalkonium Chloride | 0.01% |
| Polysorbate 80 | 0.1% |
| NaOH/HCl | pH 7.02 |

The Compound (0.09 g), benzalkonium chloride (0.03 g), polysorbate 80 (0.15 g) can be mixed together in water (1.23 g) and ball milled for approximately 4 h. A hydroxypropylmethylcellulose vehicle can be prepared by mixing 2% aqueous hydroxypropylmethylcellulose (40 g), sodium chloride (1.28 g), dibasic sodium phosphate (0.32 g), disodium edetate (0.016 g), sodium chloride (1.28 g) and water (35 g) together and the pH adjusted to 7.4 by the addition of 1N HCl (250 µL). A portion of this vehicle (1.5 mL) can be added to the mixture containing the Compound to furnish the desired suspension.

EXAMPLE 16

Ophthalmic Solution

| Ingredient | Concentration (wt %) |
|---|---|
| 3,4-Dihydro-4-ethylamino-2-methyl-2H-thieno[3,2-e]-1,2-thiazine-6-sulfonamide-1,1-dioxide hydrochloride (Compound) | 2.0% |
| Hydroxyethylcellulose | 0.5% |
| Monobasic Sodium Phosphate | 0.13% |
| Dibasic Sodium Phosphate | 0.01% |
| Benzalkonium Chloride | 0.01% |
| Disodium Edetate | 0.01% |
| Purified Water | q.s. |
| NaCl (Osmolality = 282 mOsm) | 0.4% |
| HCl/NaOH | pH 5.0 |

The Compound (0.06 g) and sodium chloride (0.014 g) were mixed together in water (1.44 g) and the pH of the solution was adjusted to 5.02 by the addition of 1N NaOH (10 µL). The hydroxyethylcellulose vehicle was prepared by mixing together monobasic sodium phosphate (0.26 g), dibasic sodium phosphate (0.02 g) and disodium edetate (0.02 g) in water (96.7 g). The benzalkonium chloride (2.0 g) and hydroxyethylcellulose were added to the mixture and the pH was adjusted to 5.01 by the addition of 1N HCl (100 µl) A portion of this vehicle (1.5 g) was added to the solution containing the compound and the pH was adjusted to 5.03 by the addition of 1N NaOH (10 µL).

EXAMPLE 17

Ophthalmic Gel

| Ingredient | Concentration (wt %) |
|---|---|
| 3,4-Dihydro-2-methyl-4-(2-methyl)propyl-amino-2H-thieno[3,2-e]-1,2-thiazine-6-sulfonamide-1,1-dioxide hydrochloride (Compound) | 1.0% |
| Mannitol | 3.6% |
| Benzalkonium Chloride | 0.01% |
| Carbopol | 3.0% |
| HCl/NaOH | pH 5.0 |
| Purified Water | q.s. |

The mannitol (0.18 g), benzalkonium chloride (0.05 mL), Compound (0.1 g) and carbopol (0.15 g) can all be added to water (4.3 mL) and mixed well. The pH can be adjusted to pH 5.0 and purified water (q.s. to 5 mL) can be added and mixed well to form a gel.

EXAMPLE 18

Ophthalmic Solution

| Ingredient | Concentration (wt %) |
|---|---|
| R-(+)-4-Ethylamino-3,4-dihydro-2-methyl-2H-thieno[3,2-e]-1,2-thiazine-6-sulfonamide-1,1-dioxide hydrochloride (Compound) | 2.27% |
| Hydroxypropylmethylcellulose | 3.3% |
| Sodium Acetate Dihydrate | 0.1% |
| Mannitol (Osmolality - 282 mOsm) | 2.44% |
| Benzalkonium Chloride | 0.01% |
| Disodium Edetate | 0.01% |
| Purified Water | q.s. |
| HCl/NaOH | pH 5.0 |

The sodium acetate (0.2 g). disodium edta (0.02 g), benzylalkonium chloride (2.1 g of a 1% solution) and mannitol (5.32 g) were dissolved in water for injection (115 mL). The pH was adjusted to 5.0 with 1N sodium hydroxide and the final volume was adjusted to 117 mL with water for injection. Hydroxypropylmethylcellulose (83.0 g of an 8% solution) was mixed with the 117 mL of the acetate buffer solution to furnish the vehicle. To prepare the final formulation, 0.068 g of the Compound was diluted with vehicle to make 3.0 mL total volume and the pH was adjusted to 5.0 with 1N sodium hydroxide (5 µL).

EXAMPLE 19

Ophthalmic Solution

| Ingredient | Concentration (wt %) |
|---|---|
| R-(+)4-Ethylamino-3,4-dihydro-2-(2-methoxy)ethyl-2H-thieno[3,2-e]-1,2-thiazine-6-sulfonamide-1,1-dioxide hydrochloride (Compound) | 1.69% |
| Hydroxypropylmethylcellulose | 3.0% |
| Sodium Acetate trihydrate | 0.1% |
| Mannitol (Osmolality = 317 mOsm) | 2.4% |
| Benzalkonium Chloride | 0.01% |
| Disodium Edetate | 0.01% |
| Purified Water | q.s. |

-continued

| Ingredient | Concentration (wt %) |
|---|---|
| HCl/NaOH | pH 6.4 |

The above ingredients were mixed together in substantially the same manner as described in Example 18 to furnish the ophthalmic solution.

EXAMPLE 20

Ophthalmic Solution

| Ingredient | Concentration (wt %) |
|---|---|
| R-(+)-3,4-Dihydro-2-(2-methoxy)ethyl-4-propylamino-2H-thieno[3,2-e]-1,2-thiazine-6-sulfonamide-1,1-dioxide hydrochloride (Compound) | 2.19% |
| Hydroxypropylmethylcellulose | 3.0% |
| Sodium Acetate trihydrate | 0.1% |
| Mannitol (Osmolality = 288 mOsm) | 2.4% |
| Benzalkonium Chloride | 0.01% |
| Disodium Edetate | 0.01% |
| Purified Water | q.s. |
| HCl/NaOH | pH 5.0 |

The above ingredients were mixed together in substantially the same manner as described in Example 18 to furnish the ophthalmic solution.

EXAMPLE 21

Ophthalmic Suspension

| Ingredient | Concentration (wt %) |
|---|---|
| (+)4-Ethylamino-3,4-dihydro-2-(3-methoxy)propyl-2H-thieno[3,2-e]-1,2-thiazine-6-sulfonamide-1,1-dioxide hydrochloride (Compound) | 2.0% |
| Hydroxypropylmethylcellulose | 0.5% |
| Dibasic Sodium Phosphate | 0.2% |
| Disodium Edetate | 0.01% |
| Sodium Chloride | 0.8% |
| Purified Water | q.s |
| Benzalkonium Chloride | 0.01% |
| Polysorbate 80 | 0.1% |
| NaOH/HCl | pH 7.1 |

The above ingredients can be mixed together in substantially the same manner as described in Example 15 to furnish the ophthalmic suspension.

EXAMPLE 22

Ophthalmic Suspension

| Ingredient | Concentration (wt %) |
|---|---|
| R-(+)-3,4-Dihydro-2-(4-methoxybutyl)-4-propylamino-2H-thieno[3,2-e]-1,2-thiazine-6-sulfonamide 1,1-dioxide (Compound) | 2.0% |
| Hydroxypropylmethylcellulose | 3.0% |
| Dibasic Sodium Phosphate | 0.2% |
| Sodium Chloride | 0.7% |
| Disodium EDTA | 0.01% |
| Polysorbate 80 | 0.05 |
| Benzalkonium Chloride Solution | 0.01% + 5% xs |
| Sodium Hydroxide | q.s. pH = 7.2 |
| Hydrochloric Acid | q.s. pH = 7.2 |
| Water for Injection | q.s. 100% |

The above ingredients were mixed together using a procedure similar to that described in Example 15 to furnish the ophthalmic suspension.

EXAMPLE 23

Ophthalmic Suspension

| Ingredient | Concentration (wt %) |
|---|---|
| R-(+)-3,4-Dihydro-2-(4-methoxybutyl)-4-propylamino-2H-thieno[3,2-e]-1,2-thiazine-6-sulfonamide 1,1-dioxide (Compound) | 2.0% |
| Hydroxypropylmethylcellulose | 3.0% |
| Sodium acetate (trihydrate) | 0.1% |
| Mannitol | 4.1% |
| Disodium EDTA | 0.01% |
| Benzalkonium Chloride Solution | 0.01% + 5% xs |
| Sodium Hydroxide | q.s. pH = 5.0 |
| Hydrochloric Acid | q.s. pH = 5.0 |
| Water for Injection | q.s. 100% |

The above ingredients were mixed together in a manner similar to the same general procedure described in Example 15 to furnish the ophthalmic suspension.

EXAMPLE 24

Ophthalmic Suspension

| Ingredient | Concentration (wt %) |
|---|---|
| R-(+)-3,4-Dihydro-2-(4-methoxybutyl)-4-propylamino-2H-thieno[3,2-e]-1,2-thiazine-6-sulfonamide 1,1-dioxide (Compound) | 2.0% |
| Carbomer 934P | 0.5% |
| Sodium Chloride | 0.4% |
| Mannitol | 2.4% |
| Disodium EDTA | 0.01% |
| Polysorbate 80 | 0.05% |
| Benzalkonium Chloride Solution | 0.01% + 5% xs |
| Sodium Hydroxide | q.s. pH = 7.2 |
| Hydrochloric Acid | q.s. pH = 7.2 |
| Water for Injection | q.s. 100% |

The above ingredients were mixed together using a method similar to the same general procedure described in Example 15 to furnish the ophthalmic suspension.

EXAMPLE 25

Ophthalmic Suspension

| Ingredient | Concentration (wt %) |
|---|---|
| R-(+)-4-Ethylamino-3,4-dihydro-2-(2-methylpropyl)-2H-thieno[3,2-e]-1,2-thiazine-6-sulfonamide 1,1-dioxide hydrochloride (Compound) | 2.0% |
| Carbomer 934P | 0.5% |
| Sodium Chloride | 0.4% |
| Mannitol | 2.4% |
| Disodium EDTA | 0.01% |
| Polysorbate 80 | 0.05% |
| Benzalkonium Chloride Solution | 0.01% + 5% xs |
| Sodium Hydroxide | q.s. pH = 7.2 |
| Hydrochloric Acid | q.s. pH = 7.2 |
| Water for Injection | q.s. 100% |

The above ingredients can be mixed together using a method similar to the same general procedure described in Example 15 to furnish the ophthalmic suspension.

EXAMPLE 26

Ophthalmic Suspension

| Ingredient | Concentration (wt %) |
|---|---|
| R-(+)-Ethylamino-3,4-dihydro-2-(4-methoxybutyl)-2H-thieno[3,2-e]-1,2-thiazine-6-sulfonamide 1,1-dioxide (Compound) | 2.0% |
| Carbomer 934P | 0.5% |
| Sodium Chloride | 0.4% |
| Mannitol | 2.4% |
| Disodium EDTA | 0.01% |
| Polysorbate 80 | 0.05% |
| Benzalkonium Chloride Solution | 0.01% + 5% xs |
| Sodium Hydroxide | q.s. pH = 7.2 |
| Hydrochloric Acid | q.s. pH = 7.2 |
| Water for Injection | q.s. 100% |

The above ingredients can be mixed together using a method similar to the same general procedure described in Example 15 to furnish the ophthalmic suspension.

We claim:

1. A compound of the formula

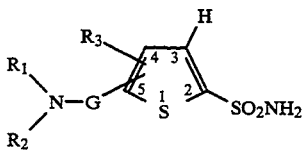

or a pharmaceutically acceptable salt thereof wherein:
$R^1$ and $R^3$ are each saturated carbon atoms joined together to form a ring of 6 members in which said carbon atoms can be unsubstituted or substituted optionally with $R_4$;

$R_2$ is H; $C_{1-8}$ alkyl; $C_{2-8}$ alkyl substituted with OH, $NR_5R_6$, halogen, $C_{1-4}$ alkoxy, $C_{2-4}$alkoxy$C_{1-4}$alkoxy, OC(=O)$R_7$, or C(=O)$R_7$; $C_{3-7}$ alkenyl unsubstituted or substituted optionally with OH, $NR_5R_6$, or $C_{1-4}$ alkoxy; $C_{3-7}$alkynyl unsubstituted or substituted optionally with $C_1$-$C_3$alkyl, $C_1$-$C_3$halo alkyl, OH, $NR_5R_6$, or $C_{1-4}$alkoxy; $C_{1-3}$ alkyl substituted with phenyl or $R_{10}$ either of which can be unsubstituted or substituted optionally with $C_1$-$C_3$alkyl, $C_1$-$C_3$halo alkyl, OH, $(CH_2)_nNR_5R_6$, halogen, $C_{1-4}$ alkoxy, $C_{1-4}$ haloalkoxy, C(=O)$R_7$, S(=O)$_mR_8$ or SO$_2NR_5R_6$, wherein m is 0–2 and n is 0–2; $C_{2-4}$ alkoxy substituted optionally with $NR_5R_6$, halogen, $C_{1-4}$alkoxy, or C(=O)$R_7$; phenyl or $R_{10}$ either of which can be unsubstituted or substituted optionally with OH, $(CH_2)_nNR_5R_6$, halogen, $C_{1-4}$ alkoxy, $C_{1-4}$ haloalkoxy, C(=O)$R_7$, S(=O)$_mR_8$ or SO$_2NR_5R_6$, wherein m is 0–2 and n is 0–2;

$R_4$ is OH; $C_{1-4}$ alkyl unsubstituted or substituted optionally with OH, $NR_5R_6$, halogen, $C_{1-4}$ alkoxy or C(=O)$R_7$; $C_{1-4}$ alkoxy; $C_{2-4}$ alkoxy substituted optionally with OH, $NR_5R_6$, halogen, $C_{1-4}$ alkoxy or C(=O)$R_7$; $NR_5R_6$; phenyl or $R_{10}$ either of which can be unsubstituted or substituted optionally with OH, $(CH_2)_nNR_5R_6$, halogen, $C_{1-4}$ alkoxy, $C_{1-4}$ haloalkoxy, C(=O)$R_7$, S(=O)$_mR_8$ or SO$_2NR_5R_6$, wherein m is 0–2 and n is 0–2;

$R_5$ & $R_6$ are the same or different and are H; $C_{1-4}$ alkyl; $C_{2-4}$ alkyl substituted optionally with OH, halogen, $C_{1-4}$ alkoxy or C(=O)$R_7$; $C_{1-4}$ alkoxy; $C_{2-4}$ alkoxy substituted optionally with OH, halogen, $C_{1-4}$ alkoxy or C(=O)$R_7$; $C_{3-7}$ alkenyl unsubstituted or substituted optionally with OH, $NR_5R_6$, or $C_{1-4}$ alkoxy; $C_{3-7}$ alkynyl unsubstituted or substituted optionally with OH, $NR_5R_6$, or $C_{1-4}$ alkoxy; $C_{1-2}$alkyl$C_{3-5}$cycloalkyl; C(=O)$R_7$ or $R_5$ and $R_6$ can be joined to form a ring selected from the group consisting of pyrrolidine, oxazolidine, thiomorpholine, thiomorpholine 1,1 dioxide, morpholine, piperazine, and thiazolidine 1,1-dioxide, which can be unsubstituted or substituted optionally on carbon with OH, (=O), halogen, $C_{1-4}$ alkoxy, C(=O)$R_7$, $C_{1-6}$ alkyl, $C_{1-6}$ alkyl substituted optionally with OH, halogen, $C_{1-4}$ alkoxy, C(=O)$R_7$ or on nitrogen with $C_{1-4}$ alkoxy, C(=O)$R_7$, S(=O)$_mR_8$, $C_{1-6}$ alkyl or $C_{2-6}$ alkyl substituted optionally with OH, halogen, $C_{1-4}$ alkoxy, C(=O)$R_7$ or on sulfur by (=O)$_m$, wherein m is 0–2;

$R_7$ is $C_{1-8}$ alkyl; substituted optionally with OH, $NR_5R_6$, halogen, $C_{1-4}$ alkoxy or C(=O)$R_9$; $C_{1-4}$ alkoxy; $C_{2-4}$alkoxy substituted optionally with OH, $NR_5R_6$, halogen or $C_{1-4}$ alkoxy; $NR_5R_6$; or phenyl or $R_{10}$ either of which can be unsubstituted or substituted optionally with OH, halogen, $C_{1-3}$ alkyl, $C_{1-3}$ haloalkoxy, $(CH_2)_nNR_5R_6$, S(=O)$_mR_8$ or SO$_2NR_5R_6$, wherein n is 0 or 1 and m is 0–2;

$R_8$ is $C_{1-4}$ alkyl; $C_{2-4}$ alkyl substituted optionally with OH, $NR_5R_6$, halogen, $C_{1-4}$ alkoxy or C(=O)$R_7$;

$R_9$ is $C_{1-4}$ alkyl; $C_{1-4}$ alkoxy; amino, $C_{1-3}$ alkylamino, or di-$C_{1-3}$ alkylamino;

$R_{10}$ is a monocyclic ring system selected from the group consisting of furan, thiophene, pyrrole, pyrazole, imidazole, triazole, tetrazole, oxazole, isoxazole, isothiazole, thiazole, thiadiazole, pyridine, pyrimidine, pyridazine, and pyrazine; and G is SO$_2$.

2. The compound of Claim 1 wherein: $R_3$ is in the 4-position and GNR$_1R_2$ is in the 5-position.

3. The compound of Claim 2 wherein:
$R_2$ is H; $C_{1-8}$ alkyl; $C_{2-8}$ alkyl substituted with OH, $NR_5R_6$, halogen, $C_{1-4}$ alkoxy, $C_{2-4}$alkoxy$C_{1-4}$alkoxy, OC(=O)$R_7$, or C(=O)$R_7$; $C_{3-7}$ alkenyl unsubstituted or substituted optionally with OH, $NR_5R_6$, or $C_{1-4}$ alkoxy; $C_{3-7}$ alkynyl unsubstituted or substituted optionally with $C_1$-$C_3$alkyl, $C_1$-$C_3$halo alkyl, OH, $NR_5R_6$, or $C_{1-4}$ alkoxy; $C_{1-3}$ alkyl substituted with phenyl or $R_{10}$ either of which can be unsubstituted or substituted optionally with $C_1$-$C_3$alkyl, $C_1$-$C_3$Halo alkyl, OH, $(CH_2)_nNR_5R_6$, halogen, $C_{1-4}$ alkoxy, $C_{1-4}$ haloalkoxy, C(=O)$R_7$, S(=O)$_mR_8$ or SO$_2NR_5R_6$, wherein m is 0–2 and n is 0–2; $C_{2-4}$ alkoxy substituted optionally with $NR_5R_6$, halogen, $C_{1-4}$alkoxy, or C(=O)$R_7$; phenyl or $R_{10}$ either of which can be unsubstituted or substituted optionally with OH, $(CH_2)_nNR_5R_6$, halogen, $C_{1-4}$ alkoxy, $C_{1-4}$ haloalkoxy, C(=O)$R_7$, S(=O)$_mR_8$ or SO$_2NR_5R_6$, wherein m is 0–2 and n is 0–2.

4. The compound of Claim 3 wherein:
$R_2$ is $C_{1-8}$ alkyl; $C_{2-8}$ alkyl substituted with OH, $NR_5R_6$, halogen, $C_{1-2}$ alkoxy, $C_{2-4}$alkoxy$C_{1-4}$alkoxy, OC(=O)$R_7$, or C(=O)$R_7$; $C_{3-7}$alkenyl unsubstituted or substituted optionally with OH, $NR_5R_6$, or $C_{1-4}$ alkoxy; phenyl, or $R_{10}$, unsubstituted or substituted optionally with $C_1$-$C_3$alkyl, $C_1$-$C_3$halo alkyl, OH, $(CH_2)_nNR_5R_6$, halogen, $C_{1-4}$ alkoxy, $C_{1-4}$ haloalkoxy, C(=O)$R_7$, S(=O)$_mR_8$ or SO$_2NR_5R_6$, wherein m is 0–2 and n is 0–2; $C_{1-3}$ alkyl substituted with phenyl or $R_{10}$ either of which can be unsubstituted or substituted optionally with $C_1$–$C_3$alkyl, $C_1$–$C_3$halo alkyl OH, $(CH_2)_nNR_5R_6$, halogen, $C_{1-4}$ alkoxy, $C_{1-4}$ haloalkoxy, $C(=O)R_7$, $S(=O)_mR_8$ or $SO_2NR_5R_6$, wherein m is 0–2 and n is 0–2.

5. The compound of Claim 4 wherein:

$R_4$ is OH; $C_{1-4}$ alkoxy; $C_{2-4}$ alkoxy substituted optionally with OH, $NR_5R_6$, halogen, $C_{1-4}$ alkoxy or $C(=O)R_7$; or $NR_5R_6$; phenyl, or $R_{10}$ unsubstituted or substituted optionally with OH, $(CH_2)_nNR_5R_6$, halogen, $C_{1-4}$ alkoxy, $C_{1-4}$ haloalkoxy, $C(=O)R_7$, $S(=O)_mR_8$ or $SO_2NR_5R_6$, wherein m is 0–2 and n is 0–2.

6. The compound of Claim 1 wherein:

$R_4$ is OH; $C_{1-4}$ alkoxy; $C_{2-4}$ alkoxy substituted optionally with OH, $NR_5R_6$, halogen, $C_{1-4}$ alkoxy or $C(=O)R_7$; or $NR_5R_6$; phenyl, or $R_{10}$, unsubstituted or substituted optionally with OH, $(CH_2)_nNR_5R_6$, halogen, $C_{1-4}$ alkoxy, $C_{1-4}$ haloalkoxy, $C(=O)R_7$, $S(=O)_mR_8$ or $SO_2NR_5R_6$, wherein m is 0–2 and n is 0–2.

7. A compound selected from the group consisting of:

R-(+)-4-Ethylamino-3,4-dihydro-2-(3-methoxy)propyl-2H-thieno 1,2-thiazine-6-sulfonamide-1,1-dioxide;

(R)-4-Ethylamino-3,4-dihydro-2-(3-methoxyphenyl)-2H-thieno-1,2-thiazine-6-sulfonamide 1,1-dioxide;

(R)-4-Ethylamino-2-(4-hydroxy-phenyl)-3,4-dihydro-2H-thieno-1,2-thiazine-6-sulfonamide 1,1-dioxide;

(R)-4-Ethylamino-3,4-dihydro-2-(3-hydroxy-phenyl)-2H-thieno-1,2-thiazine-6-sulfonamide 1,1-dioxide;

(R)-4-Ethylamino-3,4-dihydro-2-(4-hydroxy-phenylmethyl)-2H-thieno-1,2-thiazine-6-sulfonamide 1,1-dioxide;

(R)-4-Ethylamino-3,4-dihydro-2-(3-methoxy-phenylmethyl)-2H-thieno-1,2-thiazine-6-sulfonamide 1,1-dioxide;

R-(+)-3,4-Dihydro-2-(4-methoxybutyl)-4-propylamino-2H-thieno-1,2-thiazine-6-sulfonamide 1,1-dioxide;

R-(+)-4-Ethylamino-3,4-dihydro-2-(4-methoxybutyl)-2H-thieno-1,2-thiazine-6-sulfonamide 1,1-dioxide;

R-(+)-4-Ethylamino-3,4-dihydro-2-(2-methylpropyl)-2H-thieno-1,2-thiazine-6-sulfonamide 1,1-dioxide;

R-(+)-4-Ethylamino-3,4-dihydro-2-(6-hydroxyhexyl)-2H-thieno-1,2-thiazine-6-sulfonamide 1,1-dioxide;

(R)-3,4-Dihydro-2-(3-hydroxypropyl)-4-(2-methylpropyl)amino-2H-thieno -1,2-thiazine-6-sulfonamide 1,1-dioxide;

(R)-4-Ethylamino-3,4-dihydro-2-(3-hydroxy-phenylmethyl)-2H-thieno-1,2-thiazine-6-sulfonamide 1,1 dioxide;

(R)-3,4-Dihydro-2-(3-methoxy-phenyl)-4-(2-methylpropyl)amino-2H-thieno-1,2-thiazine-6-sulfonamide 1,1 dioxide;

(R)-3,4-Dihydro-2-(4-hydroxy-phenyl)-4-(2-methylpropyl)amino-2H-thieno-1,2-thiazine-6-sulfonamide 1,1 dioxide;

(R)-3,4-Dihydro-2-(3-methoxy-phenyl)-4-propylamino-2H-thieno-1,2-thiazine-6-sulfonamide 1,1 dioxide;

(R)-3,4-Dihydro-2-(3-hydroxy-phenyl)-4-propylamino-2H-thieno-1,2-thiazine-6-sulfonamide 1,1 dioxide;

(R)-3,4-Dihydro-2-(3-hydroxy-phenyl)-4-(2-methylpropyl)amino-2H-thieno-1,2-thiazine-6-sulfonamide 1,1 dioxide;

(R)-3,4-Dihydro-2-(4-methoxybutyl)-4-(2-methylpropyl)amino-2H-thieno-1,2-thiazine-6-sulfonamide 1,1 dioxide;

(R)-3,4-Dihydro-2-(3-methoxypropyl)-4-(2-methylpropyl)amino-2H-thieno-1,2-thiazine-6-sulfonamide 1,1 dioxide;

(R)-4-Cyclopropylmethylamino-3,4-dihydro-2-(2-propenyl)-2H-thieno-1,2-thiazine-6-sulfonamide 1,1 dioxide;

(R)-4-Cyclopropylmethylamino-3,4-dihydro-2-(4-methoxybutyl)-2H-thieno-1,2-thiazine-6-sulfonamide 1,1 dioxide;

(R)-4-Cyclopropylmethylamino-3,4-dihyro-2-(3-methoxypropyl)-2H-thieno-1,2-thiazine-6-sulfonamide 1,1 dioxide;

(R)-4-Cyclopropylmethylamino-3,4-dihydro-2-propyl-2H-thieno-1,2-thiazine-6-sulfonamide 1,1 dioxide;

(R)-3,4-Dihydro-2-(2-methylpropyl)-4-(2-methylpropyl)amino-2H-thieno-1,2-thiazine-6-sulfonamide 1,1 dioxide;

(R)-4-Cyclopropylmethylamino-3,4-dihydro-2-(2-methylpropyl)-2H-thieno-1,2-thiazine-6-sulfonamide 1,1 dioxide;

(R)-3,4-Dihydro-4-(2-methylpropyl)amino-2-propyl-2H-thieno-1,2-thiazine-6-sulfonamide 1,1 dioxide;

(R)-3,4-Dihydro-2-(4-hydroxybutyl)-4-(2-methylpropyl)amino-2H-thieno-1,2-thiazine-6-sulfonamide 1,1-dioxide;

(R)-3,4-Dihydro-2-(4-hydroxybutyl)-4-propylamino-2H-thieno-1,2-thiazine-6-sulfonamide 1,1-dioxide.

8. A formulation for controlling intraocular pressure comprising a therapeutically effective amount of the compound of Claim 1 in a pharmaceutically acceptable carrier.

9. A formulation for controlling intraocular pressure comprising a therapeutically effective amount of the compound of Claim 7 in a pharmaceutically acceptable carrier.

10. The formulation of Claim 8 wherein the compound concentration is between 0.1 and 10% by weight.

11. The formulation of Claim 9 wherein the compound concentration is between 0.1 and 10% by weight.

12. The formulation of Claim 10 wherein the compound concentration is between 0.1 and 10% by weight.

13. A method for controlling intraocular pressure which comprises topically administering to the affected eye a therapeutically effective amount of the compound of Claim 1.

14. A method for controlling intraocular pressure which comprises topically administering to the affected eye a therapeutically effective amount of the compound of Claim 7.

* * * * *

UNITED STATES PATENT AND TRADEMARK OFFICE
CERTIFICATE OF CORRECTION

PATENT NO. : 5,378,703

DATED : January 3, 1995

INVENTOR(S) : Dean, et al.

It is certified that error appears in the above-identified patent and that said Letters Patent is hereby corrected as shown below:

Column 46, line 3, change "... (=0)$R_7$ or $R_5$ ..." to "... (=O)$R_7$ or $R_5$ ..."

Column 47, line 24, insert [3,2-e] between "thieno" and "1".

Column 47, line 27, insert [3,2-e] between "thieno" and "-".

Column 47, line 30, insert [3,2-e] between "thieno" and "-".

Column 47, line 32, insert [3,2-e] between "thieno" and "-".

Column 47, line 34, insert [3,2-e] between "thieno" and "-".

Column 47, line 37, insert [3,2-e] between "thieno" and "-".

Column 47, line 40, insert [3,2-e] between "thieno" and "-".

Column 47, line 43, insert [3,2-e] between "thieno" and "-".

Column 47, line 46, insert [3,2-e] between "thieno" and "-".

Column 47, line 49, insert [3,2-e] between "thieno" and "-".

Column 47, line 52, insert [3,2-e] between "thieno" and "-".

Column 47, line 55, insert [3,2-e] between "thieno" and "-".

Column 47, line 58, insert [3,2-e] between "thieno" and "-".

Column 47, line 61, insert [3,2-e] between "thieno" and "-".

Column 48, line 2, insert [3,2-e] between "thieno" and "-".

Column 48, line 5, insert [3,2-e] between "thieno" and "-".

UNITED STATES PATENT AND TRADEMARK OFFICE
CERTIFICATE OF CORRECTION

PATENT NO. : 5,378,703
DATED : January 3, 1995
INVENTOR(S) : Dean, et al.

It is certified that error appears in the above-identified patent and that said Letters Patent is hereby corrected as shown below:

Column 48, line 8, insert [3,2-e] between "thieno" and "-".

Column 48, line 11, insert [3,2-e] between "thieno" and "-".

Column 48, line 14, insert [3,2-e] between "thieno" and "-".

Column 48, line 17, insert [3,2-e] between "thieno" and "-".

Column 48, line 20, insert [3,2-e] between "thieno" and "-".

Column 48, line 23, insert [3,2-e] between "thieno" and "-".

Column 48, line 26, insert [3,2-e] between "thieno" and "-".

Column 48, line 29, insert [3,2-e] between "thieno" and "-".

Column 48, line 32, insert [3,2-e] between "thieno" and "-".

Column 48, line 35, insert [3,2-e] between "thieno" and "-".

Column 48, line 37, insert [3,2-e] between "thieno" and "-".

Column 48, line 40, insert [3,2-e] between "thieno" and "-".

Signed and Sealed this

Twenty-ninth Day of April, 1997

Attest:

BRUCE LEHMAN

*Attesting Officer*     *Commissioner of Patents and Trademarks*